(12) United States Patent
Zhu et al.

(10) Patent No.: US 6,919,194 B2
(45) Date of Patent: Jul. 19, 2005

(54) **METHOD FOR CLONING AND EXPRESSION OF TTH111II RESTRICTION ENDONUCLEASE-METHYLASE IN *E. COLI***

(75) Inventors: Zhenyu Zhu, Beverly, MA (US); Derek Robinson, Boxford, MA (US); Jack Benner, South Hamilton, MA (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 364 days.

(21) Appl. No.: 10/338,731

(22) Filed: Jan. 8, 2003

(65) Prior Publication Data

US 2004/0132129 A1 Jul. 8, 2004

(51) Int. Cl.[7] .............................. C12N 9/22; C12N 15/55
(52) U.S. Cl. ................. 435/199; 435/320.1; 435/252.3; 536/23.2
(58) Field of Search ........................... 435/320.1, 252.3; 536/23.2

(56) References Cited

U.S. PATENT DOCUMENTS

| 5,200,333 A | 4/1993 | Wilson | ................ | 435/172.3 |
| 5,498,535 A | 3/1996 | Fomenkov et al. | ...... | 435/172.3 |

OTHER PUBLICATIONS

Roberts and Macelis, Nucl. Acids Res. 27:312–313 (1999).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, 2000–01, p. 220.
Matsudaira, J. Biol. Chem., 262:10035–10038 (1987).
Waite–Reese, et al., J. Bacteriology, 173:5207–5219 (1991).

*Primary Examiner*—Charles L. Patterson, Jr.
(74) *Attorney, Agent, or Firm*—Gregory D. Williams; Harriet M. Strimpel

(57) ABSTRACT

The present invention relates to recombinant DNA which encodes the Tth111II restriction endonuclease-methylase fusion protein (Tth111IIRM), expression of Tth111II restriction endonuclease-methylase fusion protein in *E. coli* cells containing the recombinant DNA, and purification of Tth111II endonuclease-methylase fusion protein to near homogeneity.

5 Claims, 10 Drawing Sheets

Figure 1

1. AACTGGATTGACCTGTACACCCATCTAAAACAGGAGTCCCCTGGTTCTTCAAC
   (SEQ ID NO:3)

2. AACTGGATTGATCTGTATACCCATCTAAAACAAGAAGTTCCCTGGTTCTTCAAC
   (SEQ ID NO:4)

3. AACTGGATTGATCTGTATACCCATCTAAAACAGGAAGTTCCGTGGTTTTCAAC
   (SEQ ID NO:5)

4. AACTGGATAGATCTGTACACCCATCTAAAACAAGAAGTCCCCTGGTTCTTCAAC
   (SEQ ID NO:6)

5. AACTGGATAGATCTGTACACCCATCTAAAACAGAGAGGTCCCTTGGTTCTTCAAC
   (SEQ ID NO:7)

6. AACTGGATCGATCTGTACACCCATCTAAAACAAGAAGTCCCCTGGTTTTTCAAT
   (SEQ ID NO:8)

7. AACTGGATAGATCTCTACACCCATCTAAAACAGGAGGTCCCGTGGTTCTTCAAC
   (SEQ ID NO:9)

Figure 1 - continued

8. AATTGGATAGACCTGTACACCCCATCTAAAACAGAGAGGTTCCCTTGGTTCTTTAAC
   (SEQ ID NO:10)

9. AATTGGATAGACCTGTACACCCCATCTAAAACAGGAGGTCCCCTGGTTCTTTAAT
   (SEQ ID NO:11)

10. AATTGGATAGACCTATACACCCCATCTAAAACAGGAAGTGCCCTGGTTTTTCAAT
    (SEQ ID NO:12)

11. AATTGGATCGACCTGTACACCCCATCTAAAACAGGAGGTCCCGTGGTTTTTCAAC
    (SEQ ID NO:13)

12. AATTGGATAGATCTCTACACCCCATCTAAAACAGGAGGTCCCCTTGGTTCTTCAAC
    (SEQ ID NO:14)

13. AATTGGATAGACCTGTACACCCCATCTAAAACAAGAGAGGTCCCCCTGGTTCTTTAAC
    (SEQ ID NO:15)

Figure 1 - continued

14. AATTGGATAGATCTGTATACCCCATCTAAAACAGGAAGTCCCCTTGGTTTTTCAAC
    (SEQ ID NO:16)

15. AATTGGATAGACCTCTACACCCATCTAAAACAGGAGGTCCCCTTGGTTCTTCAAC
    (SEQ ID NO:17)

16. AATTGGATCGATCTGTACACCCATCTAAAACAAGAAGTCCCCTGGTTCTTTAAC
    (SEQ ID NO:18)

CON: AAYTGGATNGAYCTNTAYACCCATCTAAAACARGARGTNCCNTGGTTYTTYAAY
    (SEQ ID NO:19)

WT: AACTGGATCGATCTTTACACCCATCTAAAACAAGAGAGGTCCCCTTGGTTTTTAAT
    (SEQ ID NO:20)

Figure 2

```
      ATGAACTGGATCGATCTTTACACCCATCTAAAACAAGAGGTCCCTTGGTTTTTTAATTCC
  1   ---------+---------+---------+---------+---------+---------+   60
      TACTTGACCTAGCTAGAAATGTGGGTAGATTTTGTTCTCCAGGGAACCAAAAAATTAAGG
       M  N  W  I  D  L  Y  T  H  L  K  Q  E  V  P  W  F  F  N  S
      GTCCGTCTCGCAGCCAGCCAAGCCCATAACGAGGCCGAGTTTGAGAGTCGGATAAACAAT
 61   ---------+---------+---------+---------+---------+---------+  120
      CAGGCAGAGCGTCGGTCGGTTCGGGTATTGCTCCGGCTCAAACTCTCAGCCTATTTGTTA
       V  R  L  A  A  S  Q  A  H  N  E  A  E  F  E  S  R  I  N  N
      GCAATTGAGCGCTTGGCTCAGAAGTTGGGTGTTCAGCTGCTTTTCCGGGAACAATATACG
121   ---------+---------+---------+---------+---------+---------+  180
      CGTTAACTCGCGAACCGAGTCTTCAACCCACAAGTCGACGAAAAGGCCCTTGTTATATGC
       A  I  E  R  L  A  Q  K  L  G  V  Q  L  L  F  R  E  Q  Y  T
      CTGGCCACTGGCCGCGCTGATGCTGTGTACAACCGTCTGGTGATAGAATACGAGCCACCC
181   ---------+---------+---------+---------+---------+---------+  240
      GACCGGTGACCGGCGCGACTACGACACATGTTGGCAGACCACTATCTTATGCTCGGTGGG
       L  A  T  G  R  A  D  A  V  Y  N  R  L  V  I  E  Y  E  P  P
      GGTTCTTTGCGGCCAAATTTGAAACACAGCCACACTCAGCATGCGGTGCGGCAGGTCATG
241   ---------+---------+---------+---------+---------+---------+  300
      CCAAGAAACGCCGGTTTAAACTTTGTGTCGGTGTGAGTCGTACGCCACGCCGTCCAGTAC
       G  S  L  R  P  N  L  K  H  S  H  T  Q  H  A  V  R  Q  V  M
      AACTACATTGAGGAGTTATCCAGAGCGGAAAGGCATGACCGCGACCGCCTGCTGGGGGTC
301   ---------+---------+---------+---------+---------+---------+  360
      TTGATGTAACTCCTCAATAGGTCTCGCCTTTCCGTACTGGCGCTGGCGGACGACCCCCAG
       N  Y  I  E  E  L  S  R  A  E  R  H  D  R  D  R  L  L  G  V
      GTCTTCGACGGCCACTACTTCATCTTTGTCCGCTACCATGAGGGGCACTGGATCGTAGAA
361   ---------+---------+---------+---------+---------+---------+  420
      CAGAAGCTGCCGGTGATGAAGTAGAAACAGGCGATGGTACTCCCCGTGACCTAGCATCTT
       V  F  D  G  H  Y  F  I  F  V  R  Y  H  E  G  H  W  I  V  E
      GAGCCCCTGGAGGTGAATCCGGCGTCGTGTGAGCGCTTCCTGCGTTCTCTCTTCTCCCTT
421   ---------+---------+---------+---------+---------+---------+  480
      CTCGGGGACCTCCACTTAGGCCGCAGCACACTCGCGAAGGACGCAAGAGAGAAGAGGGAA
       E  P  L  E  V  N  P  A  S  C  E  R  F  L  R  S  L  F  S  L
      TCTTCGGGCCGGGCGCTGATTCCCGAGAACCTGGTGGAGGACTTCGGGAGCCAGAACGAC
481   ---------+---------+---------+---------+---------+---------+  540
      AGAAGCCCGGCCCGCGACTAAGGGCTCTTGGACCACCTCCTGAAGCCCTCGGTCTTGCTG
       S  S  G  R  A  L  I  P  E  N  L  V  E  D  F  G  S  Q  N  D
      CTCAGCCGCCAGGCCACCCGTGCCCTCTACCACGCGCTGCAGGGTCATACCAGTGATCTG
541   ---------+---------+---------+---------+---------+---------+  600
      GAGTCGGCGGTCCGGTGGGCACGGGAGATGGTGCGCGACGTCCCAGTATGGTCACTAGAC
       L  S  R  Q  A  T  R  A  L  Y  H  A  L  Q  G  H  T  S  D  L
      ACCGCCCGCCTCTTTGTCCAGTGGCAAATCTTCTTCGGCGAGACGGCCGGTGCCGATGCT
601   ---------+---------+---------+---------+---------+---------+  660
      TGGCGGGCGGAGAAACAGGTCACCGTTTAGAAGAAGCCGCTCTGCCGGCCACGGCTACGA
       T  A  R  L  F  V  Q  W  Q  I  F  F  G  E  T  A  G  A  D  A
      GCGGGAGGCGAACTAAAGCACAAGAGTGAACTGCTTGCCTTTGCCCGCGGCATGGGGCTG
661   ---------+---------+---------+---------+---------+---------+  720
      CGCCCTCCGCTTGATTTCGTGTTCTCACTTGACGAACGGAAACGGGCGCCGTACCCCGAC
       A  G  G  E  L  K  H  K  S  E  L  L  A  F  A  R  G  M  G  L
      CGGGGCAGCCGGATAGACATGCCCCGCTTCCTCTTTGCCCTGCACACGTACTTCTCCTTC
721   ---------+---------+---------+---------+---------+---------+  780
      GCCCCGTCGGCCTATCTGTACGGGGCGAAGGAGAAACGGGACGTGTGCATGAAGAGGAAG
       R  G  S  R  I  D  M  P  R  F  L  F  A  L  H  T  Y  F  S  F
      CTGGTCAAAAACATCGCCCGCCTGGTGCTCCAGGCCTATGCGGGTGGCGGGCTGGGCACC
781   ---------+---------+---------+---------+---------+---------+  840
      GACCAGTTTTTGTAGCGGGCGGACCACGAGGTCCGGATACGCCCACCGCCCGACCCGTGG
       L  V  K  N  I  A  R  L  V  L  Q  A  Y  A  G  G  G  L  G  T
```

Figure 2 (continued)

```
     ACGCCCCTAACCACCATCGCCAACCTGGAAGGCGAGGCCCTGCGCCGGGAACTGCAAAAC
841  ---------+---------+---------+---------+---------+---------+ 900
     TGCGGGGATTGGTGGTAGCGGTTGGACCTTCCGCTCCGGGACGCGGCCCTTGACGTTTTG
      T  P  L  T  T  I  A  N  L  E  G  E  A  L  R  R  E  L  Q  N

CTGGAAAGCGGCGGACTTTTCCGTACCCTGGGCCTAAAGAACCTGCTGGAGGGTGACTTC
901  ---------+---------+---------+---------+---------+---------+ 960
     GACCTTTCGCCGCCTGAAAAGGCATGGGACCCGGATTTCTTGGACGACCTCCCACTGAAG
      L  E  S  G  G  L  F  R  T  L  G  L  K  N  L  L  E  G  D  F

TTCGCCTGGTACCTGGACGCCTGGAACCCGGAAGTGGAAGAAGCCCTGCGCCAGGTGCTG
961  ---------+---------+---------+---------+---------+---------+ 1020
     AAGCGGACCATGGACCTGCGGACCTTGGGCCTTCACCTTCTTCGGGACGCGGTCCACGAC
      F  A  W  Y  L  D  A  W  N  P  E  V  E  E  A  L  R  Q  V  L

GCCCGCCTGGCCGAGTACAACCCGGCCACCGTGCAGGACGACCCCCACAGCGCCCGCGAC
1021 ---------+---------+---------+---------+---------+---------+ 1080
     CGGGCGGACCGGCTCATGTTGGGCCGGTGGCACGTCCTGCTGGGGGTGTCGCGGGCGCTG
      A  R  L  A  E  Y  N  P  A  T  V  Q  D  D  P  H  S  A  R  D

CTGCTGAAAAAGCTCTACCACTACCTCCTGCCGCGGGACATCCGCCACGACCTGGGCGAG
1081 ---------+---------+---------+---------+---------+---------+ 1140
     GACGACTTTTTCGAGATGGTGATGGAGGACGGCGCCCTGTAGGCGGTGCTGGACCCGCTC
      L  L  K  K  L  Y  H  Y  L  L  P  R  D  I  R  H  D  L  G  E

TTCTACACCCCCGACTGGCTGGCCGAGCGTCTGCTCAACCAGCTGGGTGAACCCTGGTTC
1141 ---------+---------+---------+---------+---------+---------+ 1200
     AAGATGTGGGGGCTGACCGACCGGCTCGCAGACGAGTTGGTCGACCCACTTGGGACCAAG
      F  Y  T  P  D  W  L  A  E  R  L  L  N  Q  L  G  E  P  W  F

ATCATGCCCCCGGGGAACCACCCGCCCAGGGGCTTGCCCGACAAGCGCCTGCTGGACCCG
1201 ---------+---------+---------+---------+---------+---------+ 1260
     TAGTACGGGGGCCCCTTGGTGGGCGGGTCCCCGAACGGGCTGTTCGCGGACGACCTGGGC
      I  M  P  P  G  N  H  P  P  R  G  L  P  D  K  R  L  L  D  P

GCCTGCGGCTCCGGCACCTTCCCGGTGCTGGCCATCCGCGCCCTCAAGGTCAACTGCTTC
1261 ---------+---------+---------+---------+---------+---------+ 1320
     CGGACGCCGAGGCCGTGGAAGGGCCACGACCGGTAGGCGCGGGAGTTCCAGTTGACGAAG
      A  C  G  S  G  T  F  P  V  L  A  I  R  A  L  K  V  N  C  F

CTGGCTGGCTTCTCCGAGGCTGACACCCTGGAGGTTATCCTGAACAGCGTGGTGGGCATT
1321 ---------+---------+---------+---------+---------+---------+ 1380
     GACCGACCGAAGAGGCTCCGACTGTGGGACCTCCAATAGGACTTGTCGCACCACCCGTAA
      L  A  G  F  S  E  A  D  T  L  E  V  I  L  N  S  V  V  G  I

GACCTCAACCCCTTGGCTGTGACCGCAGCCCGGGTCAACTACCTGCTGGCCATCGCCGAC
1381 ---------+---------+---------+---------+---------+---------+ 1440
     CTGGAGTTGGGGAACCGACACTGGCGTCGGGCCCAGTTGATGGACGACCGGTAGCGGCTG
      D  L  N  P  L  A  V  T  A  A  R  V  N  Y  L  L  A  I  A  D

CTGCTCCCTTACCGCCGCCGGGAGGTGGAAATTCCGGTCTATCTCGCCGACAGCATACTT
1441 ---------+---------+---------+---------+---------+---------+ 1500
     GACGAGGGAATGGCGGCGGCCCTCCACCTTTAAGGCCAGATAGAGCGGCTGTCGTATGAA
      L  L  P  Y  R  R  R  E  V  E  I  P  V  Y  L  A  D  S  I  L

ACGCCGGCCCGCGGGGAAGGGCTCTTCGCCCAGAACCGCCGCATCCTGGAGACCGCGGTC
1501 ---------+---------+---------+---------+---------+---------+ 1560
     TGCGGCCGGGCGCCCCTTCCCGAGAAGCGGGTCTTGGCGGCGTAGGACCTCTGGCGCCAG
      T  P  A  R  G  E  G  L  F  A  Q  N  R  R  I  L  E  T  A  V

GGCCCCCTGCCCGTGCCCGAGGTGATTAACAGCCGCGCTAAGATGGAACGGCTCACCGAC
1561 ---------+---------+---------+---------+---------+---------+ 1620
     CCGGGGGACGGGCACGGGCTCCACTAATTGTCGGCGCGATTCTACCTTGCCGAGTGGCTG
      G  P  L  P  V  P  E  V  I  N  S  R  A  K  M  E  R  L  T  D

CTGCTTGAAGAGTACGTCCGCGGGGATTTCTCCACCGAGGCCTTCCTTGCCCGGGCCAAA
1621 ---------+---------+---------+---------+---------+---------+ 1680
     GACGAACTTCTCATGCAGGCGCCCCTAAAGAGGTGGCTCCGGAAGGAACGGGCCCGGTTT
      L  L  E  E  Y  V  R  G  D  F  S  T  E  A  F  L  A  R  A  K

AAGGAAATCCCCGACCTGGCCGATGCCCTCCATGCCGACGAAGTGATCACCGGACTCTAC
1681 ---------+---------+---------+---------+---------+---------+ 1740
     TTCCTTTAGGGGCTGGACCGGCTACGGGAGGTACGGCTGCTTCACTAGTGGCCTGAGATG
      K  E  I  P  D  L  A  D  A  L  H  A  D  E  V  I  T  G  L  Y
```

Figure 2 (continued)

```
        GAGAGGTTGCGCGACCTCCACCGCCAGGGGCTAGATGGCATCTGGGCCCGGGTGCTCAAG
1741    ---------+---------+---------+---------+---------+---------+  1800
        CTCTCCAACGCGCTGGAGGTGGCGGTCCCCGATCTACCGTAGACCCGGGCCCACGAGTTC
         E  R  L  R  D  L  H  R  Q  G  L  D  G  I  W  A  R  V  L  K

AACGCTTTCATGCCCCTCTTCCTGGAACCCTTTGACTACGTGGTGGGCAATCCGCCCTGG
1801    ---------+---------+---------+---------+---------+---------+  1860
        TTGCGAAAGTACGGGGAGAAGGACCTTGGGAAACTGATGCACCACCCGTTAGGCGGGACC
         N  A  F  M  P  L  F  L  E  P  F  D  Y  V  V  G  N  P  P  W

ATCAACTGGGAAAGCTTGCCCCAGGCCTACCGGGAGCAAACGGCCGAGTTATGGACATGY
1861    ---------+---------+---------+---------+---------+---------+  1920
        TAGTTGACCCTTTCGAACGGGGTCCGGATGGCCCTCGTTTGCCGGCTCAATACCTGTACR
         I  N  W  E  S  L  P  Q  A  Y  R  E  Q  T  A  E  L  W  T  C

TACGGCCTCTTCGTCCATTCCGGCATGGATACCATCCTGGGCAAGGGCAAAAAGGACGCC
1921    ---------+---------+---------+---------+---------+---------+  1980
        ATGCCGGAGAAGCAGGTAAGGCCGTACCTATGGTAGGACCCGTTCCCGTTTTTCCTGCGG
         Y  G  L  F  V  H  S  G  M  D  T  I  L  G  K  G  K  K  D  A

TCCACCCTGATGACCTACGCCGTGGCCGACCGCTTCTTGAAAGAGGGCGGCAAACTGGGC
1981    ---------+---------+---------+---------+---------+---------+  2040
        AGGTGGGACTACTGGATGCGGCACCGGCTGGCGAAGAACTTTCTCCCGCCGTTTGACCCG
         S  T  L  M  T  Y  A  V  A  D  R  F  L  K  E  G  G  K  L  G

TTCCTCATCACCCAGAGCGTCTGGAAAACTGGGGCTGGGCAGGGCTTCCGCCGTTTCCGT
2041    ---------+---------+---------+---------+---------+---------+  2100
        AAGGAGTAGTGGGTCTCGCAGACCTTTTGACCCCGACCCGTCCCGAAGGCGGCAAAGGCA
         F  L  I  T  Q  S  V  W  K  T  G  A  G  Q  G  F  R  R  F  R

ATCGGAGAAAACGGCCCCCATTTGCGCGTGCTACACGTGGACGACCTCTCCAGCCTGCAA
2101    ---------+---------+---------+---------+---------+---------+  2160
        TAGCCTCTTTTGCCGGGGGTAAACGCGCACGATGTGCACCTGCTGGAGAGGTCGGACGTT
         I  G  E  N  G  P  H  L  R  V  L  H  V  D  D  L  S  S  L  Q

GTCTTTGAAGGAGCCAGCACACGCACCAGCGCCTTCGTCCTGCAGAAGGGCCGGCCCCCC
2161    ---------+---------+---------+---------+---------+---------+  2220
        CAGAAACTTCCTCGGTCGTGTGCGTGGTCGCGGAAGCAGGACGTCTTCCCGGCCGGGGGG
         V  F  E  G  A  S  T  R  T  S  A  F  V  L  Q  K  G  R  P  P

CGCTACCCGGTGCCCTACACTTACTGGAAGAAGACGACCAAAGGCGAGGGGCTGGACTAC
2221    ---------+---------+---------+---------+---------+---------+  2280
        GCGATGGGCCACGGGATGTGAATGACCTTCTTCTGCTGGTTTCCGCTCCCCGACCTGATG
         R  Y  P  V  P  Y  T  Y  W  K  K  T  T  K  G  E  G  L  D  Y

GACAGCACCCTGGGCGAGGTGATGGAACAGACCAAACGTCTTCGGTTCCACGCCGTGCCG
2281    ---------+---------+---------+---------+---------+---------+  2340
        CTGTCGTGGGACCCGCTCCACTACCTTGTCTGGTTTGCAGAAGCCAAGGTGCGGCACGGC
         D  S  T  L  G  E  V  M  E  Q  T  K  R  L  R  F  H  A  V  P

GTGGACCCGGACGACCTCACCAGCCCCTGGCTCACCGCCCGCCGCAGGGCCCTGTACTCC
2341    ---------+---------+---------+---------+---------+---------+  2400
        CACCTGGGCCTGCTGGAGTGGTCGGGGACCGAGTGGCGGGCGGCGTCCCGGGACATGAGG
         V  D  P  D  D  L  T  S  P  W  L  T  A  R  R  R  A  L  Y  S

GTGCGCAAGGTGCTGGGGACGTCGGAGTACCGGGCGTACGAAGGAGCCAACAGTGGAGGA
2401    ---------+---------+---------+---------+---------+---------+  2460
        CACGCGTTCCACGACCCCTGCAGCCTCATGGCCCGCATGCTTCCTCGGTTGTCACCTCCT
         V  R  K  V  L  G  T  S  E  Y  R  A  Y  E  G  A  N  S  G  G

GCCAACGGCATCTACTGGCTGGAAATCCTGGCCGAGCGACCGGACGGGCTGGTGGTGGTG
2461    ---------+---------+---------+---------+---------+---------+  2520
        CGGTTGCCGTAGATGACCGACCTTTAGGACCGGCTCGCTGGCCTGCCCGACCACCACCAC
         A  N  G  I  Y  W  L  E  I  L  A  E  R  P  D  G  L  V  V  V

CGCAATGTGACTGAGGGGGCTAAACGGGAGGTGGAGGGCATTACCACCGAACTGGAGCCC
2521    ---------+---------+---------+---------+---------+---------+  2580
        GCGTTACACTGACTCCCCCGATTTGCCCTCCACCTCCCGTAATGGTGGCTTGACCTCGGG
         R  N  V  T  E  G  A  K  R  E  V  E  G  I  T  T  E  L  E  P

GACCTGCTCTACCCCCTGCTGCGCGGCCGGGATGTGCGCCGCTGGTATGCACAACCATCT
2581    ---------+---------+---------+---------+---------+---------+  2640
        CTGGACGAGATGGGGGACGACGCGCCGGCCCTACACGCGGCGACCATACGTGTTGGTAGA
         D  L  L  Y  P  L  L  R  G  R  D  V  R  R  W  Y  A  Q  P  S
```

Figure 2 (continued)

```
         TTGCACATCCTCATGGTGCAGGACCCCAAGACGCGGCGGGGCATAGACGAGCAGGTGCTC
2641     ---------+---------+---------+---------+---------+---------+ 2700
         AACGTGTAGGAGTACCACGTCCTGGGGTTCTGCGCCGCCCCGTATCTGCTCGTCCACGAG
          L  H  I  L  M  V  Q  D  P  K  T  R  R  G  I  D  E  Q  V  L
         CAGAAGCGCTACCCCAAGACCTGGGCCTACCTCAAGCGCTTTGAGGCGGTGCTGCGGGAG
2701     ---------+---------+---------+---------+---------+---------+ 2760
         GTCTTCGCGATGGGGTTCTGGACCCGGATGGAGTTCGCGAAACTCCGCCACGACGCCCTC
          Q  K  R  Y  P  K  T  W  A  Y  L  K  R  F  E  A  V  L  R  E
         CGTTCCGGCTTCAGGCGCTACTTTACCCGCAAGGACAGGAACGGCCGCATGGTGGAAACC
2761     ---------+---------+---------+---------+---------+---------+ 2820
         GCAAGGCCGAAGTCCGCGATGAAATGGGCGTTCCTGTCCTTGCCGGCGTACCACCTTTGG
          R  S  G  F  R  R  Y  F  T  R  K  D  R  N  G  R  M  V  E  T
         GGCCCCTTCTACTCTATGTTTAACGTCGGCGACTACACCTTCGCGCCGTGGAAGGTGGTG
2821     ---------+---------+---------+---------+---------+---------+ 2880
         CCGGGGAAGATGAGATACAAATTGCAGCCGCTGATGTGGAAGCGCGGCACCTTCCACCAC
          G  P  F  Y  S  M  F  N  V  G  D  Y  T  F  A  P  W  K  V  V
         TGGCGATACGTGGCTTCGGATTTTATTGTTGCTGTAGTAGGTCCTGCTTCAGATGAGAAG
2881     ---------+---------+---------+---------+---------+---------+ 2940
         ACCGCTATGCACCGAAGCCTAAAATAACAACGACATCATCCAGGACGAAGTCTACTCTTC
          W  R  Y  V  A  S  D  F  I  V  A  V  V  G  P  A  S  D  E  K
         CCCGTTGTTCCTAACGAAAAGCTTATGTTAGTGCCTGTTGAAGACGATAATGAGGCTTTC
2941     ---------+---------+---------+---------+---------+---------+ 3000
         GGGCAACAAGGATTGCTTTTCGAATACAATCACGGACAACTTCTGCTATTACTCCGAAAG
          P  V  V  P  N  E  K  L  M  L  V  P  V  E  D  D  N  E  A  F
         TACTTGTGTGGGGTTCTGAACTCTTCTCCAATCCGTTTTGCGGTCCAAAGTTTCTTTGTC
3001     ---------+---------+---------+---------+---------+---------+ 3060
         ATGAACACACCCCAAGACTTGAGAAGAGGTTAGGCAAAACGCCAGGTTTCAAAGAAACAG
          Y  L  C  G  V  L  N  S  S  P  I  R  F  A  V  Q  S  F  F  V
         CAAACACAAATTGCCCCTCACGTGCTTCAAAAACTTTGCATTCCCAGATATGAACCGAAC
3061     ---------+---------+---------+---------+---------+---------+ 3120
         GTTTGTGTTTAACGGGGAGTGCACGAAGTTTTTGAAACGTAAGGGTCTATACTTGGCTTG
          Q  T  Q  I  A  P  H  V  L  Q  K  L  C  I  P  R  Y  E  P  N
         ACTGACCATCAAAATCGCATCGCCCACCTCTCCCGCCGCGCCCACGAGCTGGCCCCGGCG
3121     ---------+---------+---------+---------+---------+---------+ 3180
         TGACTGGTAGTTTTAGCGTAGCGGGTGGAGAGGGCGGCGCGGGTGCTCGACCGGGGCCGC
          T  D  H  Q  N  R  I  A  H  L  S  R  R  A  H  E  L  A  P  A
         GCCTACAATGGGGACAAAGCGGCCCGGGCCGAACTGCGGCGGGTGGAAGAGGAGATTGAC
3181     ---------+---------+---------+---------+---------+---------+ 3240
         CGGATGTTACCCCTGTTTCGCCGGGCCCGGCTTGACGCCGCCCACCTTCTCCTCTAACTG
          A  Y  N  G  D  K  A  A  R  A  E  L  R  R  V  E  E  E  I  D
         CGGGCCGCGGCCCAACTCTGGGGCCTGACGGAGGAGGAACTGGCCGAGATTCGGCGGAGT
3241     ---------+---------+---------+---------+---------+---------+ 3300
         GCCCGGCGCCGGGTTGAGACCCCGGACTGCCTCCTCCTTGACCGGCTCTAAGCCGCCTCA
          R  A  A  A  Q  L  W  G  L  T  E  E  E  L  A  E  I  R  R  S
         TTGGAGGAGTTGCGGGGGTAC
3301     ---------+---------+-  3321
         AACCTCCTCAACGCCCCCATC
          L  E  E  L  R  G  *
```

METHOD FOR CLONING AND EXPRESSION OF TTH111II RESTRICTION ENDONUCLEASE-METHYLASE IN E. COLI

BACKGROUND OF THE INVENTION

The present invention relates to recombinant DNA encoding the Tth111II restriction endonuclease methylase fusion protein (RM fusion protein), as well as expression of Tth111II RM fusion protein in *E. coli* cells containing the recombinant DNA.

Tth111II endonuclease is found in the strain of *Thermus thermophilus* 111 (New England Biolabs' strain collection #249 (Beverly, Mass.)). It recognizes the double-stranded DNA sequence 5'CAARCA3'N11/N9 and cleaves downstream sequence at N11 (top strand) and N9 (bottom strand) to generate a 2-base 3' overhang (/ indicates the cleavage of phosphodiester bond).

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') on DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3', respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the expressions of restriction-modification systems in bacteria enable them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985); Tsp45I: Wayne et al. *Gene* 202:83–88, (1997)).

A third approach is to select for active expression of methylase genes (methylase selection) (U.S. Pat. No. 5,200,333 and BsuRI: Kiss et al., *Nucl. Acids. Res.* 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,535; Fomenkov et al., *Nucl. Acids Res.* 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, TfiI nuclease) have been cloned by this method (U.S. Pat. No. 5,498,535). The disadvantage of this method is that sometimes positive blue clones containing a restriction endonuclease gene are difficult to culture due to the lack of the cognate methylase gene.

There are three major groups of DNA methylases based on the position and the base that is modified (C5 cytosine methylases, N4 cytosine methylases, and N6 adenine methylases). N4 cytosine and N6 adenine methylases are amino-methyltransferases (Malone et al. *J. Mol. Biol.* 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) (SEQ ID NO:1) can also make the DNA resistant to PspGI restriction digestion. Another example is that CpG methylase can modify the CG dinucioetide and make the NotI site (5'GCGGCCGC3' (SEQ ID NO:2)) refractory to NotI digestion (New England Biolabs' Catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a great commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a recombinant DNA encoding the Tth111II as well as related to methods for cloning and producing Tth111II endonuclease-methylase fusion gene from *Thermus thermophilus* 111 into *E. coli* by protein sequencing and inverse PCR amplification of the adjacent DNA containing Tth111II restriction endonuclease-methylase fusion gene (Tth111II, Tth111IIR, and Tth111IIRM are used to refer to the same protein).

Native Tth111II was purified from the native strain *Thermus thermophilus* 111 by chromatography through Heparin sepharose, QHP, Heparin TSK and Poly Cat A. The native Tth111II was purified near homogeneity, it showed only one band on the protein gel and with an apparent molecular weight of 115 kDa. The purified enzyme was sequenced to obtain the N-terminus amino acid sequence.

At first ApoI and NlaIII partial genomic DNA libraries were constructed using the cloning vector pUCKm (Km^R). No methylase positive clones were identified following the methylase selection method. No resistant clones were found in Acc65I, AseI, AvrII, BfaI, BsiWI, BsrGI, MseI, NdeI, NheI, NsiI, NspI, PstI, SacI, SalI, SpeI, SphI, XbaI, and XhoI genomic DNA libraries following Tth111II challenge and retransformation. This negative result suggested that the methylase selection was not strong enough or poor expression of the Tth111II methylase in the cloning host (it was found that the methylase domain is fused with the endonuclease domain, see below in Example I).

The N-terminus of the purified native Tth111II was sequenced, which generated the amino acid sequence of the first twenty residues. According to the amino acid sequence, two pairs of degenerated PCR primers were synthesized and PCR was performed. Direct sequencing of the PCR product with the degenerate primers failed to generate any sequences. PCR product was then phosphorylated with T4 polynucleotide kinase and ligated to the SmaI cut and CIP treated pUC19. Clones with inserts were screened and the plasmids were sequenced and all of inserts were found to be primer dimmer. Another set of PCR primers with BamHI sites incorporated were synthesized and used in PCR. PCR products were cloned into BamHI digested pUC19. Clones with inserts were screened and sequenced. The bona fide DNA coding sequence was obtained although at some nucleotide positions (at priming sites) degenerate bases still exist. Among the 60 bp coding sequence, only the non-priming region (14 bp) does not contain degenerate bases. A pair of inverse PCR primers was designed for the inverse PCR and PCR products were found in AluI, BfaI, BstUI, MspI, NlaIII, and Sau3AI digested templates. The DNA products were gel-purified and sequenced. Another two rounds of inverse PCR and sequencing resulted in the discovery of the entire open reading frame (ORF). The entire ORF was amplified and cloned into the expression vector pET28a and transformed into *E. coli* ER2744. Active clones with single copy insert with Tth111II activity were sequenced and confirmed to contain the wild type sequence.

During over-expression of the Tth111II in pET28a, two clones displayed high Tth111II activity. Further restriction analysis revealed that the clones contain one complete gene copy and a second copy with deletion in the first 6 bp including the starting codon. The duplication may contribute to the stability and higher expression level and higher Tth111II activity since the second copy with 6-bp deletion may abolish the endonuclease activity while it still maintains the methylase activity.

BRIEF DESCRIPTION OF THE DRAWINGS

FIG. 1. Nucleotide sequence of the N-terminus coding sequence of tth111IIR gene. Clones 1–16: 16 sequenced isolates (SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18). Con: consensus sequence (SEQ ID No:19), WT (SEQ ID No:20): bona fide coding sequence of the tth111IIR gene. The nucleotide in bold is 100% identity in all sequenced isolates.

FIG. 2. DNA sequence of Tth111II endonuclease-methylase gene (tth111IIR, 3321 bp) (SEQ ID NO:21) and its encoded amino acid sequence (SEQ ID NO:22).

DETAILED DESCRIPTION OF THE INVENTION

Figure 3:
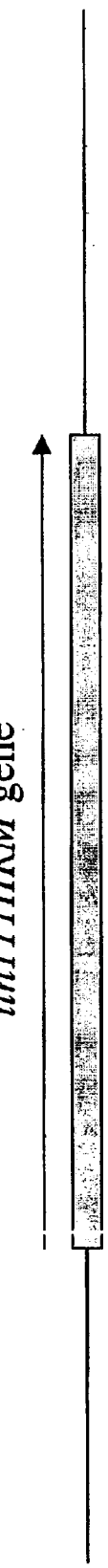
FIG. 3. Gene organization of Tth111II restriction-modification system.
Figure 4:
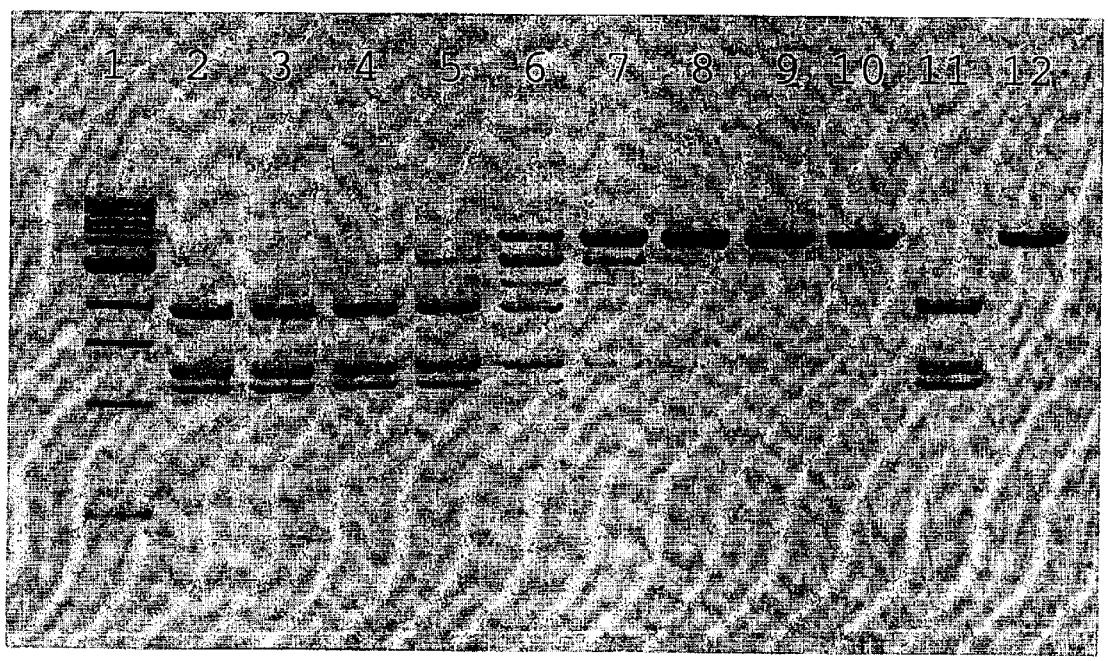
FIG. 4. Recombinant Tth111II restriction endonuclease activity. Lane 1, 1 kb DNA marker; lanes 2 to 9, substrate DNA treated with diluted fractions from heparin sepharose column containing recombinant Tth111II restriction endonuclease-methylase fusion protein; The dilution factors in lanes 2 to 9 were: 4, 8, 16, 32, 64, 128, 256, 512. Lane 10: further dilution. Lane 11: substrate DNA digested with purified native Tth111II; Lane 12: substrate DNA=EcoRI linearized pBR322.

It was very difficult to purify sufficient Tth111II endonuclease from the native strain. Starting from 60 grams of cells and purification through heparin sepharose, Q HP, Heparin TSK and poly Cat A chromatography columns, Tth111II was purified to >95% purity. This procedure yielded less than 250 units of naive Tth111II. Cloning of Tth111II R coding sequence is a prerequisite for commercial production.

The cloning of tth111IIRM gene proved to be very difficult even though high-copy-number cloning vector such as pUCKm was used. Tth111II genomic DNA was partially digested with ApoI or NlaIII and DNA fragment between 3–10 kb was gel-purified and then ligated to EcoRI or SphI digested and CIP treated pUCkm. The ligated DNA was used to transform ER2502. Plasmid DNA was prepared from amplified transformants and challenged with Tth111II. Following Tth111II digestion, the DNA mixture was transformed back into *E. coli* ER2502 cells. Transformants were screened for resistance to Tth111II digestion. Out of 36 screened no true resistant clones were identified. More genomic DNA libraries were constructed. Genomic DNA was digested with Acc65I, AseI, AvrII, BfaI, BsiWI, BsrGI, MseI, NdeI, NheI, NsiI, NspI, PstI, SacI, SalI, SpeI, SphI, XbaI, and XhoI and ligated to cloning vector pUCKm with compatible ends. Following Tth111II digestion and retransformation, more clones were screened and no true Tth111II resistant clones were identified. These negative results suggested that the Tth111II challenge was not strong enough or the expression of Tth111II methylase gene was inadequate in E. coli to modify the Tth111II sites on the vector. It was concluded that the methylase selection method failed to clone the Tth111II methylase gene.

The purified Tth111II endonuclease protein was subjected to N-terminus protein sequencing. The N-terminus amino acid sequence was obtained. A pair of degenerated primers was designed based on the amino acid sequence. The first PCR attempt yielded a PCR product of 50–100 bp. Direct sequencing of the PCR product failed probably due to the primer degeneracy. After cloning and sequencing of the PCR products, it was confirmed that the amplified products were primer dimmer.

The method described herein by which the tth111IIRM gene is preferably cloned and expressed in E. coli using the following steps:

1. Purification of Native Tth111II from Thermus Thermophilus 111

Native Tth111II was purified from sixty grams of Thermus thermophilus 111 cell through four chromatographic columns: heparin sepharose, Q HP, heparin TSK, poly Cat A. After final step, the purity of Tth111II was >95%. It was a single band on the SDS-PAGE with the molecular weight of 115 kDa. ~250 units were obtained from these cells. The yield of Tth111II was 4.2 units/gram of wet cells from the native strain.

2. PCR and Inverse PCR Amplification of tth111IIRM Gene

The N-terminus of Tth111II was sequenced and the sequence of the first twenty amino acids was derived. The amino acid sequence was used for degenerate PCR primer design in order to amplify the coding sequence. A set of PCR primers was designed including the GGATCC (BamHI site) for increased cloning efficiency. A PCR attempt was carried out to amplify the coding sequence. PCR product was obtained and digested with BamHI and then cloned into BamHI digested and CIP treated pUC19. Clones with the right size insert were sequenced. Some clones contained inserts in duplicate or triplicate. 16 independent sequences were obtained. The middle 14 base pairs coding sequence contained no ambiguity, which provided the sequence basis for making inverse PCR primers. Thermus thermophilus 111 genomic DNA was digested with restriction enzymes with 4 bp recognition sequences and then self-ligated. The self-ligated DNA was used as the templates for inverse PCR. PCR products were derived from AluI, BfaI, BstUI, MspI, NlaIII, and Sau3AI templates and sequenced. Additional three rounds of inverse PCR generated the entire coding sequence. The tth111IIRM gene is 3321 bp long, encoding an 1106 amino acid protein. The predicted molecular weight of this protein is 126 kDa, which is close agreement with the native Tth111II apparent molecular weight of 115 kDa. Conserved amino acid motif analysis revealed that this protein contained nine conserved motifs of gamma type aminomethyltransferase. Tth111II endonuclease protein is a fusion of endonuclease and methylase, which belongs to the restriction endonuclease type IIG (MmeI and Eco57I like enzymes). Further inverse PCR amplification of upstream sequence (640 bp) and downstream sequence (1 kb) did not reveal any open reading frame with homology to methylase. Thus, tth111IIR gene is a stand-alone endonuclease-methylase gene.

3. Expression of tth111IIR Gene in T7 Expression Vector pET28a

Two primers were used to amplify the tth111IIR gene in PCR. An XbaI-BamHI fragment containing the tth111IIR gene was cloned into pET28a expression vector. The ligated recombinant DNA was transformed into ER2744. The $Km^R$ transformants were induced with IPTG. Recombinant Tth111II activity was detected in the supernatant of the IPTG-induced cell extracts. Plasmids were extracted from those clones with high activity. It was found the pET28a with duplicate copy insert was the clone with highest activity and stability. After sequencing the insert, it was found the first copy insert contains the wild type sequence and the second copy insert contains a deletion of 6 bp. The second copy with two codon deletions may still encode an active methylase. This clone was used for the stability test and production of the Tth111II endonuclease protein.

4. Purification of Tth111II Endonuclease

Cell extract containing the recombinant Tth111II endonuclease-methylase fusion protein was purified by heat treatment and chromatography through Heparin Sepharose and DEAE Sepharose columns.

The present invention is further illustrated by the following Example. This Example is provided to aid in the understanding of the invention and is not construed as a limitation thereof.

The references cited above and below are herein incorporated by reference.

EXAMPLE I

Cloning of Tth111II Restriction-modification System (RM Fusion) in E. coli

1. Purification of the Native Tth111II (a) 60 grams of wet Thermus thermophilus 111 cell was suspended in 3 times of column volume of starting buffer (20 mM Tris-HCl, pH 7.5, 100 mM NaCl, 6 mM β-mercaptoethanol, 1 mM EDTA, 5% glycerol), and was lysed by sonication.

(b) The cell extract was centrifuged. The first column is the 4 cm×10 cm Heparin Sepharose column. The column is eluted with a ten column volume NaCl gradient from 100 mM to 1 M. Fractions 56–60 containing Tth111II activity was collected. Pool was dialyzed against buffer (20 mM Tris-HCl, pH7.8, 50 mM NaCl, 1 mM DTT, 1 mM EDTA, 5% glycerol).

(c) The pooled protein was purified through a 24 ml Q-HP column. Fractions 28–30 around 290 mM NaCl were pooled. Pool was dialyzed against buffer (20 mM Tris-HCl, pH7.8, 50 mM NaCl, 1 mM DTT, 1 mM EDTA, 5% glycerol).

(d) Tth111II was purified through a 1.5 ml heparin TSK column. Fractions 51–53 around 600 mM NaCl were pooled. The pool volume is 60 ml.

(e) Dilute the above pool with 52 ml of the buffer (20 mM Kpi, pH 6.8, 1 mM DTT, 1 mM EDTA, 5% glycerol). The sample was loaded on a 5 ml poly cat A column. The proteins were eluted with a NaCl gradient. Fractions 44 and 45 were pooled, at ~400 mM NaCl.

Figure 5:
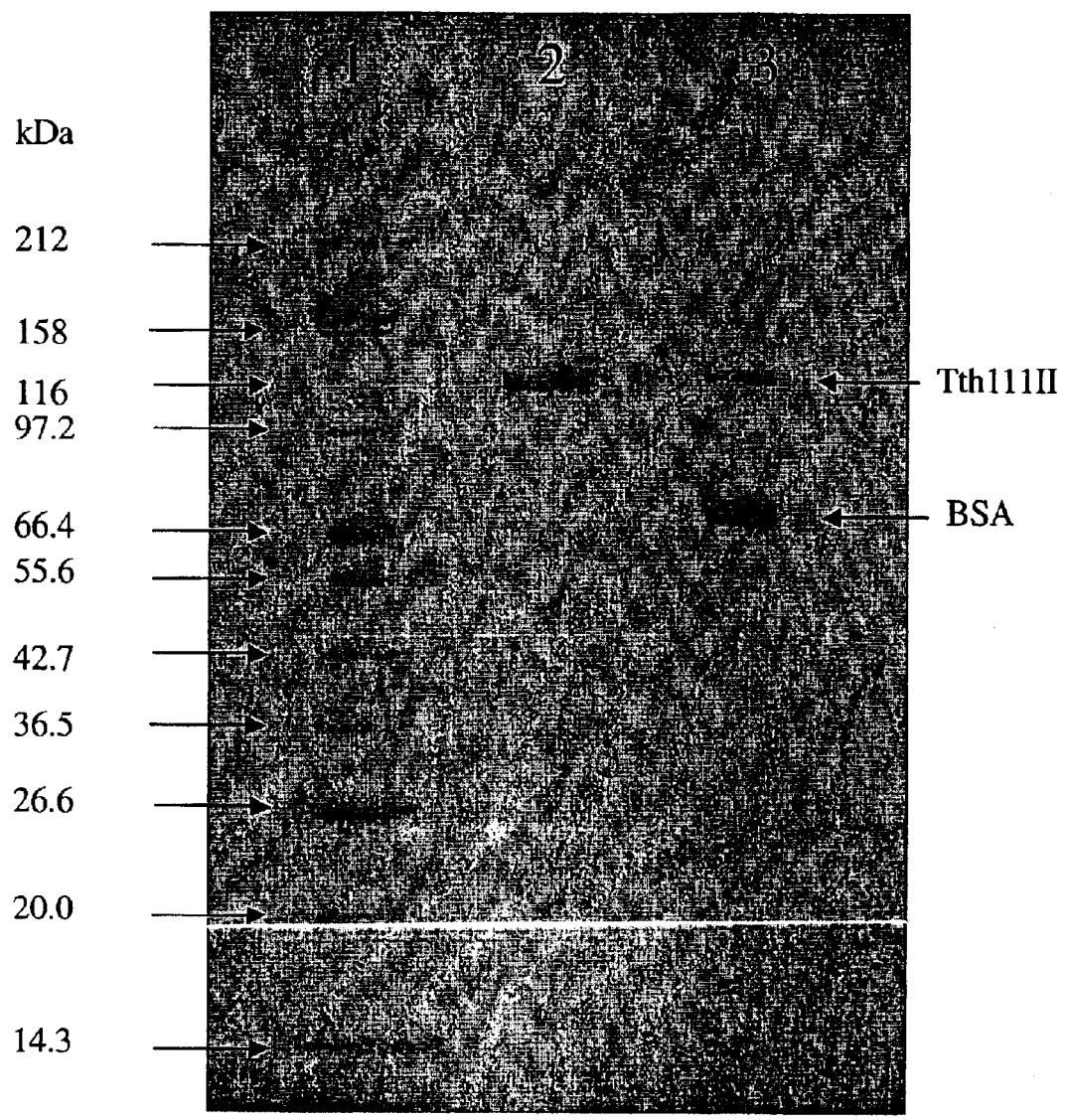
FIG. 5. Purified recombinant Tth111II restriction endonuclease-methylase fusion protein on SDS-PAG gel. Lane 1, broad range protein molecular weight marker, lane 2, purified Tth111II endonuclease-methylase fusion protein. Lane 3: purified native Tth111II with BSA.

(f) A total of 250 units Tth111II were purified. The protein consists of a single band on the SDS-PAGE. The protein has an apparent molecular weight of 115 kDa. (FIG. 5) The enzyme was stored in 50% glycerol and 200 ug/ml BSA.

2. Sequencing the N-Terminus Region of Tth111II

The purified Tth111II protein was subjected to electrophoresis and electro-blotted to a membrane (Matsudaira, J. Biol. Chem, 262:10035–10038 (1987); Waite-Reese, et al., J. Bacteriology 173:5207–5219 (1991)). The membrane was then stained with Commassie blue R-250 and the 115-kDa protein band was excised and subjected to sequential degradation in an automated Precise 494 Protein/Peptide Sequence (Applied Biosystems, Foster City, Calif.).

The N-terminus of Tth111II was sequenced and following amino acid sequence was derived:

MSNWIDLYTHLKQEVPWFFN (SEQ ID NO:23)

3. Preparation of Genomic DNA and Restriction Digestion of Genomic DNA

Genomic DNA was prepared from *Thermus thermophilus* 111 (New England Biolabs' collection #249) by the standard procedure consisting of the following steps:

(a) Cell lysis by addition of lysozyme (2 mg/ml final), sucrose (1% final), and 50 mM Tris-HCl, pH 8.0;

(b) Cell lysis by addition of 10% SDS (final concentration 0.1%);

(c) Further cell lysis by addition of 1% Triton X-100 and 62 mM EDTA, 50 mM Tris-HCl, pH 8.0;

(d) Phenol-CHCl$_3$ extraction of DNA 3 times (equal volume) and CHCl$_3$ extraction once;

(e) DNA dialysis in 4 liters of TE buffer, change 3 times; and (f) RNA removal by RNase A treatment and the genomic DNA was precipitated with 95% ethanol, washed with 70% ethanol, vacuum dried and resuspended in TE buffer.

4. PCR Amplification of N-terminus Coding Sequence

The following primers were synthesized from the N-terminal amino acid sequence:

5'-GGTGGTGGATCCAAYTGGATHGAYCTNTAYAC    (284–368) (SEQ ID NO: 24)

5'-GGTGGTGGATCCRTTRAARAACCANGGNACYTCYTG    (284–370) (SEQ ID NO: 25)

(R = A, G; Y = C, T; N = A, G, C, T; H = A, C, T)

Gradient PCR was carried out under the following condition: 95° C. 30 sec, 30–55° C. (+0.7° C. /cycle) 30 sec, 72° C. 30 sec for 35 cycles with variation in MgSO$_4$ concentration (2 mM to 10 mM) using Taq polymerase (New England Biolabs, Inc., Beverly, Mass.). PCR products were obtained in the reaction with 2, 4, 8 additional MgSO$_4$. The PCR product was digested with BamHI overnight and ligated to pUC19 cut with BamHI and CIP treated. The ligated mix was then transformed into ER2502 competent cells. Eighteen plasmids were extracted and analyzed by BamHI digestion. Fifteen out of 18 contained inserts (1, 2, 3, 4, 5, 6, 7, 9, 10 11, 12, 13, 14, 17, 18) and the inserts were sequenced using pUC universal primers. The sequencing results showed that there is a segment of 14 bp sequences without any ambiguity (FIG. 1). The priming sites contain some degenerate nucleotide sequences that resulted from the degeneracy of the PCR primers.

5. Inverse PCR Cloning and Sequencing of the Adjacent DNA

*Thermus thermophilus* 111 genomic DNA was digested with restriction enzymes with 4 bp recognition sequence to identify DNA fragments that include part or all of the tth111IIR gene or the adjacent DNA sequences. The genomic DNA was digested with AluI, BfaI, BstUI, HaeIII, HhaI, HpyCH4IV, HpyCH4V, MseI, MspI, NlaIII, RsaI, Sau3AI, TaqI, and Tsp509I respectively at 37° C. for 2 h. The restricted DNA was purified by Qiagen spin column and then used for self-ligation. Two µg DNA was ligated in 500 µl volume (2 µg DNA, 50 µl 10× ligation buffer, 2000 units T4 DNA ligase, sterile distilled water to 500 µl, 16° C. overnight). The ligated DNA was heat-treated at 65° C. for 30 min to inactivate T4 DNA ligase and 20 µl DNA was used as template for inverse PCR. The first pair of inverse PCR primers have the following sequences:

5'-ACCCATCTAAAACARGTNCCNTGGTT    (286–192) (SEQ ID NO: 26)

5'-TGTTTTAGATGGGTRTANAGRTCDATCCA    (286–244) (SEQ ID NO: 27)

(R = A, G; N = A, G, C, T, D = A, G, T)

The inverse PCR conditions were one cycle of 95° C. for 5 min, 95° C. for 30 sec, 50° C. for 1 min, 72° C. for 1 min for 35 cycles, then 72° C. for 7 min. The DNA polymerases were Taq DNA polymerase and Vent® (exo⁻) DNA polymerase. PCR products were found in the ligated templates of AluI: 350 bp, BfaI: >1500 bp, BstUI: 800 bp, HhaI: 200 bp, HpyCH4IV: >2000 bp, HpyCH4V: 200 bp, MspI: 450 bp, NlaIII: 250 bp, RsaI: 260 bp, Sau3AI: 500 bp, TaqI: 400 bp, Tsp509I: 150 bp. The PCR products were gel-purified and sequenced which generated approximately 2000 bp sequence.

The second round of inverse PCR used the following primers:

5'-ACCGGACTCTACGAGAGGTTGCGC    (286–320) (SEQ ID NO: 28)

5'-GTCGGCATGGAGGGCATCGGCCAG    (286–321) (SEQ ID NO: 29)

The genomic DNA of *Thermus thermophilus* 111 was digested by ApoI, BsrFI, MseI, NgoMIV, RsaI, SmaI, StuI, and Tsp509I, respectively, at 37° C. for 2 h. The restricted DNA was purified by Qiagen spin column and then used for self-ligation. Two µg DNA was ligated in 500 µl volume (2 µg DNA, 50 µl 10× ligation buffer, 2000 units T4 DNA ligase, sterile distilled water to 500 µl, 16° C. overnight). The ligated DNA was heat-treated at 65° C. for 30 min to inactivate T4 DNA ligase and 20 µl DNA was used as template for inverse PCR. Inverse PCR condition was 95° C. for 5 min for 1 cycle, 95° C. for 1 min, 55° C. for 1 min, 72° C. for 2 min for 35 cycles. PCR products were found in the self-ligated templates of ApoI: 800 bp, BsrFI: 750 bp, MseI: 1200 bp, NgoMIV: 750 bp, RsaI: 800 bp, SmaI: 800 bp, StuI: 700 bp, Tsp509I: 800 bp. PCR product from MseI template was gel-purified and sequenced that produced 1010 bp new sequence.

The third round of inverse PCR used the following primers:

5'-GGACAGGAACGGACCGCATGGTGG    (287–040) (SEQ ID NO: 30)

5'-TAGCGCCTGAAGCCGGAACGCTCC    (287–041) (SEQ ID NO: 31)

The genomic DNA from *Thermus thermophilus* 111 was digested by AluI, ApoI, MfeI, MscI, NspI, PvuII, and SphI, respectively, at 37° C. for 2 h. The restricted DNA was purified by Qiagen spin column and then used for self-ligation. Two μg DNA was ligated in 500 μl volume (2 μg DNA, 50 μl 10× ligation buffer, 2000 units T4 DNA ligase, sterile distilled water to 500 μl, 16° C. overnight). The ligated DNA was heat-treated at 65° C. for 30 min to inactivate T4 DNA ligase and 20 μl DNA was used as template for inverse PCR. Inverse PCR condition was 95° C. 5 min for 1 cycle, 95° C. for 1 min, 55° C. for 1 min, 72° C. for 2 min for 35 cycles. PCR products were found in the templates of AfeI: 1.8 kb, AluI: 1.1 kb, HpyCH4V 400 bp, NgoMIV: 2.8 kb, SmaI: 1.5 kb, Tsp509I: 1.6 kb. The PCR product from the AfeI template was sequenced generated ~1.7 kb new sequence.

After the third round of inverse PCR, the entire tth111IIR gene was obtained. The gene is 3321 bp in length, encoding a protein of 1106 amino acids. The predicted molecular mass of Tth111II is 126 kDa (FIG. 2). The Tth111II endonuclease is a fusion of an endonuclease domain and an amino-methylase domain. Therefore, Tth111II endonuclease gene can be referred to as tth111IIR or tth111IIRM gene.

There is no second methylase gene adjacent to Tth111IIRM gene upstream or downstream. The tth111IIRM gene is a stand-alone gene (FIG. 3). The upstream sequence has homology to a galactose binding lectin encoding gene. The downstream sequence has a low homology to cuticle collagen encoding gene.

6. Expression of tth111IIRM Gene in T7 Expression Vector pET28a

XbaI restriction site (5'TCTAGA3') was incorporated in the forward PCR primer, BamHI restriction site (5'GGATCC3') was incorporated into the reverse PCR primers for amplification of Tth111IIRM gene by PCR. The primers have the following sequences:

mutant gene with two-codon deletion. The mutant copy deleted the first 6 bp (including the start codon). The gene duplication generated the following sequence:

5' GGGGGTAG------GTGGATCGATCTTT    (SEQ ID NO: 34)

The underlined nucleotide is the end of the first copy and the italicized sequence is the beginning of the mutant copy. Clones with this type of gene duplication were more stable and produced higher Tth111II endonuclease activity in cell extract. It was more stable probably due to the deletion mutant gene may still encode a functional methylase but inactive in endonuclease activity. This clone was used in subsequent large-scale purification of Tth111II endonuclease protein.

It was noted that Tth111II recognizes the double-stranded DNA sequence 5'CAARCA3'N11/N9. Only the top DNA strand 5'CAARCA3' contains target base methylation site. The bottom strand 5'TGYTTG3' does not contain any known methylation site. It is not known how the native strain or the E. coli expression host deals with unmodified Tth111II site following DNA replication.

7. Purification of Tth111II Endonuclease

Cell extract was prepared by sonication of 4 grams of cells resuspended in 20 ml sonication buffer (50 mM Tris-HCl, pH 7.8, 10 mM β-mercaptoethanol). Cell debris was removed by centrifugation. The cell extract was heated at 65° C. for one hour to denature E. coli thermolabile proteins. Denatured proteins were removed by centrifugation. The supernatant was loaded onto a 20 ml Heparin Sepharose column. Following extensive washing with low salt buffer (20 mM Tris-HCl, pH 7.5, 50 mM NaCl, 10 mM β-mercaptoethanol, 0.1 mM EDTA), proteins were eluted

5' GGTGGTTCTAGAAATAATTTTGTTTAACTTTAAGGAGGTAAATAGAA (287–354)    (SEQ ID NO: 32)

CTGGATCGATCTTTACACCCAT 3'

5' GGTGGTGGATCCCTACCCCCGCAACTCCTCCAAACT 3'    (287–355).    (SEQ ID NO: 33)

The tth111IIRM gene was amplified by PCR using Deep Vent DNA polymerase and primers 287–354 and 287–355 under conditions of 95° C. for 1 min, 65° C. for 1 min, 72° C. for 3.5 min for 25 cycles. The PCR product was purified by Qiagen spin column and digested overnight with XbaI and BamHI. After DNA purification from low-melting agarose gel, the PCR DNA was ligated to CIP-treated pET28a with compatible ends. The ligated DNA was transformed into E. coli host ER2744 and selected for Km® transformants. Individual transformants were then picked and cultured in 10 ml LB plus Km (50 μg/ml) and induced with IPTG (0.5 mM final) for 3 h. Cell extracts of six clones were tested for Tth111II activity. All were active and two clones (#1 and #2) displayed higher activity. Plasmid digested by XbaI and BamHI showed that #1 and #2 contained tth111IIRM gene duplication. The rest of clones (#3, #4, #5, #6) contained a single-copy gene. The duplicated insert contained one copy of the wt sequence and one copy of with a NaCl gradient of 0.05 M–1 M. Fractions containing Tth111II endonuclease as determined by an activity assay were pooled and dialyzed overnight in DEAE-Sepharose loading buffer (20 mM Tris-HCl, pH 7.5, 50 mM NaCl, 10 mM β-mercaptoethanol, 0.1 mM EDTA). After dialysis, the protein mixture was loaded onto a DEAE Sepharose column equilibrated with the same buffer. Proteins were eluted with a 0.05 M–1 M NaCl gradient and those fractions containing purified Tth111II were pooled. The purified recombinant Tth111II was homogeneous in SDS-PAGE gel (>95% purity, FIG. 5). A total of 20,000 units of purified Tth111II endonuclease were obtained from 4 g of IPTG-induced cells.

The strain ER2744 [pET28a-Tth111IIRM] has been deposited under the terms and conditions of the Budapest Treaty with the American Type Culture Collection on Jan. 8, 2003 and received ATCC Accession No. PTA 4891.

What is claimed is:

1. Isolated DNA coding for the Tth111II restriction endonuclease-methylase, wherein the isolated DNA is obtainable from *Thermus thermophilus* 111.

2. A recombinant DNA vector comprising a vector into which a DNA segment encoding the Tth111II restriction endonuclease-methylase gene has been inserted.

3. Isolated DNA encoding the Tth111II restriction endonuclease-methylase, wherein the isolated DNA is obtainable from ATCC No. PTA 4891.

4. A host cell transformed by the vector of claim 2.

5. A method of producing recombinant Tth111II restriction endonuclease-methylase fusion protein comprising culturing a host cell transformed with the vector of claim 2 under conditions suitable for expression of said endonuclease-methylase.

* * * * *

UNITED STATES PATENT AND TRADEMARK OFFICE
CERTIFICATE OF CORRECTION

PATENT NO. : 6,919,194 B2
APPLICATION NO. : 10/338731
DATED : July 19, 2005
INVENTOR(S) : Jack S. Benner, II et al.

It is certified that error appears in the above-identified patent and that said Letters Patent is hereby corrected as shown below:

At column 10, line number 14, delete "5'CAARCA3'N11/N9" and insert -- 5'CAARCA3' N11/N9 --, therefor.

Signed and Sealed this
Tenth Day of May, 2011

David J. Kappos
*Director of the United States Patent and Trademark Office*

SEQUENCE LISTING

<160> NUMBER OF SEQ ID NOS: 34

<210> SEQ ID NO 1
<211> LENGTH: 5
<212> TYPE: DNA
<213> ORGANISM: Unknown
<220> FEATURE:
<223> OTHER INFORMATION: primer
<220> FEATURE:
<221> NAME/KEY: misc_feature
<222> LOCATION: (3)..(3)
<223> OTHER INFORMATION: W = A or T

<400> SEQUENCE: 1 ccwgg                                                                    5

<210> SEQ ID NO 2
<211> LENGTH: 8
<212> TYPE: DNA
<213> ORGANISM: Unknown
<220> FEATURE:
<223> OTHER INFORMATION: Nocardia otitidis-caviarum

<400> SEQUENCE: 2 gcggccgc                                                                 8

<210> SEQ ID NO 3
<211> LENGTH: 54
<212> TYPE: DNA
<213> ORGANISM: Unknown
<220> FEATURE:
<223> OTHER INFORMATION: sequence isolate

<400> SEQUENCE: 3
aactggattg acctgtacac ccatctaaaa caggaggtcc cctggttctt caac            54

<210> SEQ ID NO 4
<211> LENGTH: 54
<212> TYPE: DNA
<213> ORGANISM: Unknown
<220> FEATURE:
<223> OTHER INFORMATION: sequence isolate

<400> SEQUENCE: 4
aactggattg atctgtatac ccatctaaaa caagaagttc cctggttctt caac            54

<210> SEQ ID NO 5
<211> LENGTH: 54
<212> TYPE: DNA
<213> ORGANISM: Unknown
<220> FEATURE:
<223> OTHER INFORMATION: sequence isolate

<400> SEQUENCE: 5
aactggattg atctgtatac ccatctaaaa caggaagttc cgtggtttttt caac           54

<210> SEQ ID NO 6
<211> LENGTH: 54
<212> TYPE: DNA
<213> ORGANISM: Unknown
<220> FEATURE:
<223> OTHER INFORMATION: sequence isolate

<400> SEQUENCE: 6
aactggatag atctgtacac ccatctaaaa caagaagtcc cctggttctt caac            54

```
<210> SEQ ID NO 7
<211> LENGTH: 54
<212> TYPE: DNA
<213> ORGANISM: Unknown
<220> FEATURE:
<223> OTHER INFORMATION: sequence isolate

<400> SEQUENCE: 7
aactggatag atctgtacac ccatctaaaa caagaggtcc cttggttctt caac        54

<210> SEQ ID NO 8
<211> LENGTH: 54
<212> TYPE: DNA
<213> ORGANISM: Unknown
<220> FEATURE:
<223> OTHER INFORMATION: sequence isolate

<400> SEQUENCE: 8
aactggatcg atctctacac ccatctaaaa caagaagtcc cctggttttt caat        54

<210> SEQ ID NO 9
<211> LENGTH: 54
<212> TYPE: DNA
<213> ORGANISM: Unknown
<220> FEATURE:
<223> OTHER INFORMATION: sequence isolate

<400> SEQUENCE: 9
aactggatag atctctacac ccatctaaaa caggaggtcc cgtggttctt caac        54

<210> SEQ ID NO 10
<211> LENGTH: 54
<212> TYPE: DNA
<213> ORGANISM: unknown
<220> FEATURE:
<223> OTHER INFORMATION: sequence isolate

<400> SEQUENCE: 10
aattggatag acctgtacac ccatctaaaa caagaggttc cttggttctt taac        54

<210> SEQ ID NO 11
<211> LENGTH: 54
<212> TYPE: DNA
<213> ORGANISM: Unknown
<220> FEATURE:
<223> OTHER INFORMATION: sequence isolate

<400> SEQUENCE: 11
aattggatag acctgtacac ccatctaaaa caggaggtcc cctggttctt taat        54

<210> SEQ ID NO 12
<211> LENGTH: 54
<212> TYPE: DNA
<213> ORGANISM: Unknown
<220> FEATURE:
<223> OTHER INFORMATION: sequence isolate

<400> SEQUENCE: 12
aattggatag acctatacac ccatctaaaa caggaagtgc cctggttttt caat        54

<210> SEQ ID NO 13
<211> LENGTH: 54
<212> TYPE: DNA
<213> ORGANISM: Unknown
<220> FEATURE:
```

```
<223> OTHER INFORMATION: sequence isolate

<400> SEQUENCE: 13
aattggatcg acctgtacac ccatctaaaa caggaggtcc cgtggttttt caac          54

<210> SEQ ID NO 14
<211> LENGTH: 54
<212> TYPE: DNA
<213> ORGANISM: Unknown
<220> FEATURE:
<223> OTHER INFORMATION: sequence isolate

<400> SEQUENCE: 14
aattggatag atctctacac ccatctaaaa caggaggtcc cttggttctt caac          54

<210> SEQ ID NO 15
<211> LENGTH: 54
<212> TYPE: DNA
<213> ORGANISM: Unknown
<220> FEATURE:
<223> OTHER INFORMATION: sequence isolate

<400> SEQUENCE: 15
aattggatag acctgtacac ccatctaaaa caagaggtcc cctggttctt taac          54

<210> SEQ ID NO 16
<211> LENGTH: 55
<212> TYPE: DNA
<213> ORGANISM: Unknown
<220> FEATURE:
<223> OTHER INFORMATION: Sequence isolate

<400> SEQUENCE: 16
aattggatag atctgtatac ccatctaasa acaggaagtc ccttggtttt tcaac         55

<210> SEQ ID NO 17
<211> LENGTH: 54
<212> TYPE: DNA
<213> ORGANISM: Unknown
<220> FEATURE:
<223> OTHER INFORMATION: sequence isolate

<400> SEQUENCE: 17
aattggatag acctctacac ccatctaaaa caggaggtcc cttggttctt caac          54

<210> SEQ ID NO 18
<211> LENGTH: 54
<212> TYPE: DNA
<213> ORGANISM: Unknown
<220> FEATURE:
<223> OTHER INFORMATION: sequence isolate

<400> SEQUENCE: 18
aattggatcg atctgtacac ccatctaaaa caagaagtcc cctggttctt taac          54

<210> SEQ ID NO 19
<211> LENGTH: 54
<212> TYPE: DNA
<213> ORGANISM: Unknown
<220> FEATURE:
<223> OTHER INFORMATION: consensus sequence
<220> FEATURE:
<221> NAME/KEY: misc_feature
<222> LOCATION: (3)..(3)
<223> OTHER INFORMATION: Y = C or T
<220> FEATURE:
<221> NAME/KEY: misc_feature
```

```
<222> LOCATION: (9)..(9)
<223> OTHER INFORMATION: N = G, A, C, or T
<220> FEATURE:
<221> NAME/KEY: misc_feature
<222> LOCATION: (12)..(12)
<223> OTHER INFORMATION: Y = C or T
<220> FEATURE:
<221> NAME/KEY: misc_feature
<222> LOCATION: (15)..(15)
<223> OTHER INFORMATION: N = G, A, C or T
<220> FEATURE:
<221> NAME/KEY: misc_feature
<222> LOCATION: (18)..(18)
<223> OTHER INFORMATION: Y = C or T
<220> FEATURE:
<221> NAME/KEY: misc_feature
<222> LOCATION: (33)..(33)
<223> OTHER INFORMATION: R = A or G
<220> FEATURE:
<221> NAME/KEY: misc_feature
<222> LOCATION: (36)..(36)
<223> OTHER INFORMATION: R = A or G
<220> FEATURE:
<221> NAME/KEY: misc_feature
<222> LOCATION: (39)..(39)
<223> OTHER INFORMATION: N = G, A, C, or T
<220> FEATURE:
<221> NAME/KEY: misc_feature
<222> LOCATION: (42)..(42)
<223> OTHER INFORMATION: N = G, A, C, or T
<220> FEATURE:
<221> NAME/KEY: misc_feature
<222> LOCATION: (48)..(48)
<223> OTHER INFORMATION: Y = C or T
<220> FEATURE:
<221> NAME/KEY: misc_feature
<222> LOCATION: (51)..(51)
<223> OTHER INFORMATION: Y = C or T
<220> FEATURE:
<221> NAME/KEY: misc_feature
<222> LOCATION: (54)..(54)
<223> OTHER INFORMATION: Y = C or T

<400> SEQUENCE: 19
aaytggatng ayctntayac ccatctaaaa cargargtnc cntggttytt yaay         54

<210> SEQ ID NO 20
<211> LENGTH: 54
<212> TYPE: DNA
<213> ORGANISM: Unknown
<220> FEATURE:
<223> OTHER INFORMATION: coding sequence of the tth111IIR gene

<400> SEQUENCE: 20
aactggatcg atctttacac ccatctaaaa caagaggtcc cttggttttt taat         54

<210> SEQ ID NO 21
<211> LENGTH: 3321
<212> TYPE: DNA
<213> ORGANISM: thermus thermophilus 111
<220> FEATURE:
<221> NAME/KEY: CDS
<222> LOCATION: (1)..(3321)
<223> OTHER INFORMATION:

<400> SEQUENCE: 21 atg aac tgg atc gat ctt tac acc cat cta aaa caa gag gtc cct tgg   48
Met Asn Trp Ile Asp Leu Tyr Thr His Leu Lys Gln Glu Val Pro Trp
1               5                   10                  15 ttt ttt aat tcc gtc cgt ctc gca gcc agc caa gcc cat aac gag gcc   96
Phe Phe Asn Ser Val Arg Leu Ala Ala Ser Gln Ala His Asn Glu Ala
            20                  25                  30
```

```
gag ttt gag agt cgg ata aac aat gca att gag cgc ttg gct cag aag      144
Glu Phe Glu Ser Arg Ile Asn Asn Ala Ile Glu Arg Leu Ala Gln Lys
         35                  40                  45 ttg ggt gtt cag ctg ctt ttc cgg gaa caa tat acg ctg gcc act ggc      192
Leu Gly Val Gln Leu Leu Phe Arg Glu Gln Tyr Thr Leu Ala Thr Gly
 50                  55                  60 cgc gct gat gct gtg tac aac cgt ctg gtg ata gaa tac gag cca ccc      240
Arg Ala Asp Ala Val Tyr Asn Arg Leu Val Ile Glu Tyr Glu Pro Pro
 65                  70                  75                  80 ggt tct ttg cgg cca aat ttg aaa cac agc cac act cag cat gcg gtg      288
Gly Ser Leu Arg Pro Asn Leu Lys His Ser His Thr Gln His Ala Val
                 85                  90                  95 cgg cag gtc atg aac tac att gag gag tta tcc aga gcg gaa agg cat      336
Arg Gln Val Met Asn Tyr Ile Glu Glu Leu Ser Arg Ala Glu Arg His
            100                 105                 110 gac cgc gac cgc ctg ctg ggg gtc gtc ttc gac ggc cac tac ttc atc      384
Asp Arg Asp Arg Leu Leu Gly Val Val Phe Asp Gly His Tyr Phe Ile
        115                 120                 125 ttt gtc cgc tac cat gag ggg cac tgg atc gta gaa gag ccc ctg gag      432
Phe Val Arg Tyr His Glu Gly His Trp Ile Val Glu Glu Pro Leu Glu
130                 135                 140 gtg aat ccg gcg tcg tgt gag cgc ttc ctg cgt tct ctc ttc tcc ctt      480
Val Asn Pro Ala Ser Cys Glu Arg Phe Leu Arg Ser Leu Phe Ser Leu
145                 150                 155                 160 tct tcg ggc cgg gcg ctg att ccc gag aac ctg gtg gag gac ttc ggg      528
Ser Ser Gly Arg Ala Leu Ile Pro Glu Asn Leu Val Glu Asp Phe Gly
                165                 170                 175 agc cag aac gac ctc agc cgc cag gcc acc cgt gcc ctc tac cac gcg      576
Ser Gln Asn Asp Leu Ser Arg Gln Ala Thr Arg Ala Leu Tyr His Ala
            180                 185                 190 ctg cag ggt cat acc agt gat ctg acc gcc cgc ctc ttt gtc cag tgg      624
Leu Gln Gly His Thr Ser Asp Leu Thr Ala Arg Leu Phe Val Gln Trp
        195                 200                 205 caa atc ttc ttc ggc gag acg gcc ggt gcc gat gct gcg gga ggc gaa      672
Gln Ile Phe Phe Gly Glu Thr Ala Gly Ala Asp Ala Ala Gly Gly Glu
210                 215                 220 cta aag cac aag agt gaa ctg ctt gcc ttt gcc cgc ggc atg ggg ctg      720
Leu Lys His Lys Ser Glu Leu Leu Ala Phe Ala Arg Gly Met Gly Leu
225                 230                 235                 240 cgg ggc agc cgg ata gac atg ccc cgc ttc ctc ttt gcc ctg cac acg      768
Arg Gly Ser Arg Ile Asp Met Pro Arg Phe Leu Phe Ala Leu His Thr
                245                 250                 255 tac ttc tcc ttc ctg gtc aaa aac atc gcc cgc ctg gtg ctc cag gcc      816
Tyr Phe Ser Phe Leu Val Lys Asn Ile Ala Arg Leu Val Leu Gln Ala
            260                 265                 270 tat gcg ggt ggc ggg ctg ggc acc acg ccc cta acc acc atc gcc aac      864
Tyr Ala Gly Gly Gly Leu Gly Thr Thr Pro Leu Thr Thr Ile Ala Asn
        275                 280                 285 ctg gaa ggc gag gcc ctg cgc cgg gaa ctg caa aac ctg gaa agc ggc      912
Leu Glu Gly Glu Ala Leu Arg Arg Glu Leu Gln Asn Leu Glu Ser Gly
290                 295                 300 gga ctt ttc cgt acc ctg ggc cta aag aac ctg ctg gag ggt gac ttc      960
Gly Leu Phe Arg Thr Leu Gly Leu Lys Asn Leu Leu Glu Gly Asp Phe
305                 310                 315                 320 ttc gcc tgg tac ctg gac gcc tgg aac ccg gaa gtg gaa gaa gcc ctg     1008
Phe Ala Trp Tyr Leu Asp Ala Trp Asn Pro Glu Val Glu Glu Ala Leu
                325                 330                 335 cgc cag gtg ctg gcc cgc ctg gcc gag tac aac ccg gcc acc gtg cag     1056
Arg Gln Val Leu Ala Arg Leu Ala Glu Tyr Asn Pro Ala Thr Val Gln
            340                 345                 350
```

```
gac gac ccc cac agc gcc cgc gac ctg ctg aaa aag ctc tac cac tac      1104
Asp Asp Pro His Ser Ala Arg Asp Leu Leu Lys Lys Leu Tyr His Tyr
            355                 360                 365 ctc ctg ccg cgg gac atc cgc cac gac ctg ggc gag ttc tac acc ccc      1152
Leu Leu Pro Arg Asp Ile Arg His Asp Leu Gly Glu Phe Tyr Thr Pro
        370                 375                 380 gac tgg ctg gcc gag cgt ctg ctc aac cag ctg ggt gaa ccc tgg ttc      1200
Asp Trp Leu Ala Glu Arg Leu Leu Asn Gln Leu Gly Glu Pro Trp Phe
385                 390                 395                 400 atc atg ccc ccg ggg aac cac ccg ccc agg ggc ttg ccc gac aag cgc      1248
Ile Met Pro Pro Gly Asn His Pro Pro Arg Gly Leu Pro Asp Lys Arg
                405                 410                 415 ctg ctg gac ccg gcc tgc ggc tcc ggc acc ttc ccg gtg ctg gcc atc      1296
Leu Leu Asp Pro Ala Cys Gly Ser Gly Thr Phe Pro Val Leu Ala Ile
            420                 425                 430 cgc gcc ctc aag gtc aac tgc ttc ctg gct ggc ttc tcc gag gct gac      1344
Arg Ala Leu Lys Val Asn Cys Phe Leu Ala Gly Phe Ser Glu Ala Asp
        435                 440                 445 acc ctg gag gtt atc ctg aac agc gtg gtg ggc att gac ctc aac ccc      1392
Thr Leu Glu Val Ile Leu Asn Ser Val Val Gly Ile Asp Leu Asn Pro
450                 455                 460 ttg gct gtg acc gca gcc cgg gtc aac tac ctg ctg gcc atc gcc gac      1440
Leu Ala Val Thr Ala Ala Arg Val Asn Tyr Leu Leu Ala Ile Ala Asp
465                 470                 475                 480 ctg ctc cct tac cgc cgc cgg gag gtg gaa att ccg gtc tat ctc gcc      1488
Leu Leu Pro Tyr Arg Arg Arg Glu Val Glu Ile Pro Val Tyr Leu Ala
                485                 490                 495 gac agc ata ctt acg ccg gcc cgc ggg gaa ggg ctc ttc gcc cag aac      1536
Asp Ser Ile Leu Thr Pro Ala Arg Gly Glu Gly Leu Phe Ala Gln Asn
            500                 505                 510 cgc cgc atc ctg gag acc gcg gtc ggc ccc ctg ccc gtg ccc gag gtg      1584
Arg Arg Ile Leu Glu Thr Ala Val Gly Pro Leu Pro Val Pro Glu Val
        515                 520                 525 att aac agc cgc gct aag atg gaa cgg ctc acc gac ctg ctt gaa gag      1632
Ile Asn Ser Arg Ala Lys Met Glu Arg Leu Thr Asp Leu Leu Glu Glu
530                 535                 540 tac gtc cgc ggg gat ttc tcc acc gag gcc ttc ctt gcc cgg gcc aaa      1680
Tyr Val Arg Gly Asp Phe Ser Thr Glu Ala Phe Leu Ala Arg Ala Lys
545                 550                 555                 560 aag gaa atc ccc gac ctg gcc gat gcc ctc cat gcc gac gaa gtg atc      1728
Lys Glu Ile Pro Asp Leu Ala Asp Ala Leu His Ala Asp Glu Val Ile
                565                 570                 575 acc gga ctc tac gag agg ttg cgc gac ctc cac cgc cag ggg cta gat      1776
Thr Gly Leu Tyr Glu Arg Leu Arg Asp Leu His Arg Gln Gly Leu Asp
            580                 585                 590 ggc atc tgg gcc cgg gtg ctc aag aac gct ttc atg ccc ctc ttc ctg      1824
Gly Ile Trp Ala Arg Val Leu Lys Asn Ala Phe Met Pro Leu Phe Leu
        595                 600                 605 gaa ccc ttt gac tac gtg gtg ggc aat ccg ccc tgg atc aac tgg gaa      1872
Glu Pro Phe Asp Tyr Val Val Gly Asn Pro Pro Trp Ile Asn Trp Glu
610                 615                 620 agc ttg ccc cag gcc tac cgg gag caa acg gcc gag tta tgg aca tgy      1920
Ser Leu Pro Gln Ala Tyr Arg Glu Gln Thr Ala Glu Leu Trp Thr Cys
625                 630                 635                 640 tac ggc ctc ttc gtc cat tcc ggc atg gat acc atc ctg ggc aag ggc      1968
Tyr Gly Leu Phe Val His Ser Gly Met Asp Thr Ile Leu Gly Lys Gly
                645                 650                 655 aaa aag gac gcc tcc acc ctg atg acc tac gcc gtg gcc gac cgc ttc      2016
Lys Lys Asp Ala Ser Thr Leu Met Thr Tyr Ala Val Ala Asp Arg Phe
```

|  |  |
|---|---|
| ttg aaa gag ggc ggc aaa ctg ggc ttc ctc atc acc cag agc gtc tgg<br>Leu Lys Glu Gly Gly Lys Leu Gly Phe Leu Ile Thr Gln Ser Val Trp<br>           675                    680                      685 | 2064 |
| aaa act ggg gct ggg cag ggc ttc cgc gtt ttc cgt atc gga gaa aac<br>Lys Thr Gly Ala Gly Gln Gly Phe Arg Arg Phe Arg Ile Gly Glu Asn<br>           690                    695                      700 | 2112 |
| ggc ccc cat ttg cgc gtg cta cac gtg gac gac ctc tcc agc ctg caa<br>Gly Pro His Leu Arg Val Leu His Val Asp Asp Leu Ser Ser Leu Gln<br>705                    710                    715                    720 | 2160 |
| gtc ttt gaa gga gcc agc aca cgc acc agc gcc ttc gtc ctg cag aag<br>Val Phe Glu Gly Ala Ser Thr Arg Thr Ser Ala Phe Val Leu Gln Lys<br>                    725                    730                    735 | 2208 |
| ggc cgg ccc ccc cgc tac ccg gtg ccc tac act tac tgg aag aag acg<br>Gly Arg Pro Pro Arg Tyr Pro Val Pro Tyr Thr Tyr Trp Lys Lys Thr<br>           740                    745                      750 | 2256 |
| acc aaa ggc gag ggg ctg gac tac gac agc acc ctg ggc gag gtg atg<br>Thr Lys Gly Glu Gly Leu Asp Tyr Asp Ser Thr Leu Gly Glu Val Met<br>                    755                    760                    765 | 2304 |
| gaa cag acc aaa cgt ctt cgg ttc cac gcc gtg ccg gtg gac ccg gac<br>Glu Gln Thr Lys Arg Leu Arg Phe His Ala Val Pro Val Asp Pro Asp<br>           770                    775                    780 | 2352 |
| gac ctc acc agc ccc tgg ctc acc gcc cgc cgc agg gcc ctg tac tcc<br>Asp Leu Thr Ser Pro Trp Leu Thr Ala Arg Arg Arg Ala Leu Tyr Ser<br>785                    790                    795                    800 | 2400 |
| gtg cgc aag gtg ctg ggg acg tcg gag tac cgg gcg tac gaa gga gcc<br>Val Arg Lys Val Leu Gly Thr Ser Glu Tyr Arg Ala Tyr Glu Gly Ala<br>                    805                    810                    815 | 2448 |
| aac agt gga gga gcc aac ggc atc tac tgg ctg gaa atc ctg gcc gag<br>Asn Ser Gly Gly Ala Asn Gly Ile Tyr Trp Leu Glu Ile Leu Ala Glu<br>           820                    825                    830 | 2496 |
| cga ccg gac ggg ctg gtg gtg gtg cgc aat gtg act gag ggg gct aaa<br>Arg Pro Asp Gly Leu Val Val Val Arg Asn Val Thr Glu Gly Ala Lys<br>                    835                    840                    845 | 2544 |
| cgg gag gtg gag ggc att acc acc gaa ctg gag ccc gac ctg ctc tac<br>Arg Glu Val Glu Gly Ile Thr Thr Glu Leu Glu Pro Asp Leu Leu Tyr<br>850                    855                    860 | 2592 |
| ccc ctg ctg cgc ggc cgg gat gtg cgc cgc tgg tat gca caa cca tct<br>Pro Leu Leu Arg Gly Arg Asp Val Arg Arg Trp Tyr Ala Gln Pro Ser<br>865                    870                    875                    880 | 2640 |
| ttg cac atc ctc atg gtg cag gac ccc aag acg cgg ggc ata gac<br>Leu His Ile Leu Met Val Gln Asp Pro Lys Thr Arg Arg Gly Ile Asp<br>                    885                    890                    895 | 2688 |
| gag cag gtg ctc cag aag cgc tac ccc aag acc tgg gcc tac ctc aag<br>Glu Gln Val Leu Gln Lys Arg Tyr Pro Lys Thr Trp Ala Tyr Leu Lys<br>           900                    905                    910 | 2736 |
| cgc ttt gag gcg gtg ctg cgg gag cgt tcc ggc ttc agg cgc tac ttt<br>Arg Phe Glu Ala Val Leu Arg Glu Arg Ser Gly Phe Arg Arg Tyr Phe<br>                    915                    920                    925 | 2784 |
| acc cgc aag gac agg aac ggc cgc atg gtg gaa acc ggc ccc ttc tac<br>Thr Arg Lys Asp Arg Asn Gly Arg Met Val Glu Thr Gly Pro Phe Tyr<br>           930                    935                      940 | 2832 |
| tct atg ttt aac gtc ggc gac tac acc ttc gcg ccg tgg aag gtg gtg<br>Ser Met Phe Asn Val Gly Asp Tyr Thr Phe Ala Pro Trp Lys Val Val<br>945                    950                    955                    960 | 2880 |
| tgg cga tac gtg gct tcg gat ttt att gtt gct gta gta ggt cct gct<br>Trp Arg Tyr Val Ala Ser Asp Phe Ile Val Ala Val Val Gly Pro Ala<br>                    965                    970                    975 | 2928 |
| tca gat gag aag ccc gtt gtt cct aac gaa aag ctt atg tta gtg cct | 2976 |

-continued

```
Ser Asp Glu Lys Pro Val Val Pro Asn Glu Lys Leu Met Leu Val Pro
            980                 985                 990 gtt gaa gac gat aat gag gct ttc tac ttg tgt ggg gtt ctg aac tct    3024
Val Glu Asp Asp Asn Glu Ala Phe Tyr Leu Cys Gly Val Leu Asn Ser
            995                 1000                1005 tct cca atc cgt ttt gcg gtc caa agt ttc ttt gtc caa aca caa        3069
Ser Pro Ile Arg Phe Ala Val Gln Ser Phe Phe Val Gln Thr Gln
        1010                1015                1020 att gcc cct cac gtg ctt caa aaa ctt tgc att ccc aga tat gaa        3114
Ile Ala Pro His Val Leu Gln Lys Leu Cys Ile Pro Arg Tyr Glu
        1025                1030                1035 ccg aac act gac cat caa aat cgc atc gcc cac ctc tcc cgc cgc        3159
Pro Asn Thr Asp His Gln Asn Arg Ile Ala His Leu Ser Arg Arg
        1040                1045                1050 gcc cac gag ctg gcc ccg gcg gcc tac aat ggg gac aaa gcg gcc        3204
Ala His Glu Leu Ala Pro Ala Ala Tyr Asn Gly Asp Lys Ala Ala
        1055                1060                1065 cgg gcc gaa ctg cgg cgg gtg gaa gag gag att gac cgg gcc gcg        3249
Arg Ala Glu Leu Arg Arg Val Glu Glu Glu Ile Asp Arg Ala Ala
        1070                1075                1080 gcc caa ctc tgg ggc ctg acg gag gag gaa ctg gcc gag att cgg        3294
Ala Gln Leu Trp Gly Leu Thr Glu Glu Glu Leu Ala Glu Ile Arg
        1085                1090                1095 cgg agt ttg gag gag ttg cgg ggg tag                                3321
Arg Ser Leu Glu Glu Leu Arg Gly
        1100                1105

<210> SEQ ID NO 22
<211> LENGTH: 1106
<212> TYPE: PRT
<213> ORGANISM: thermus thermophilus 111

<400> SEQUENCE: 22

Met Asn Trp Ile Asp Leu Tyr Thr His Leu Lys Gln Glu Val Pro Trp
1               5                   10                  15

Phe Phe Asn Ser Val Arg Leu Ala Ala Ser Gln Ala His Asn Glu Ala
            20                  25                  30

Glu Phe Glu Ser Arg Ile Asn Asn Ala Ile Glu Arg Leu Ala Gln Lys
        35                  40                  45

Leu Gly Val Gln Leu Leu Phe Arg Glu Gln Tyr Thr Leu Ala Thr Gly
    50                  55                  60

Arg Ala Asp Ala Val Tyr Asn Arg Leu Val Ile Glu Tyr Glu Pro Pro
65                  70                  75                  80

Gly Ser Leu Arg Pro Asn Leu Lys His Ser His Thr Gln His Ala Val
                85                  90                  95

Arg Gln Val Met Asn Tyr Ile Glu Glu Leu Ser Arg Ala Glu Arg His
            100                 105                 110

Asp Arg Asp Arg Leu Leu Gly Val Phe Asp Gly His Tyr Phe Ile
        115                 120                 125

Phe Val Arg Tyr His Glu Gly His Trp Ile Val Glu Glu Pro Leu Glu
    130                 135                 140

Val Asn Pro Ala Ser Cys Glu Arg Phe Leu Arg Ser Leu Phe Ser Leu
145                 150                 155                 160

Ser Ser Gly Arg Ala Leu Ile Pro Glu Asn Leu Val Glu Asp Phe Gly
                165                 170                 175

Ser Gln Asn Asp Leu Ser Arg Gln Ala Thr Arg Ala Leu Tyr His Ala
            180                 185                 190
```

```
Leu Gln Gly His Thr Ser Asp Leu Thr Ala Arg Leu Phe Val Gln Trp
        195                 200                 205

Gln Ile Phe Phe Gly Glu Thr Ala Gly Ala Asp Ala Ala Gly Gly Glu
        210                 215                 220

Leu Lys His Lys Ser Glu Leu Leu Ala Phe Ala Arg Gly Met Gly Leu
225                 230                 235                 240

Arg Gly Ser Arg Ile Asp Met Pro Arg Phe Leu Phe Ala Leu His Thr
                245                 250                 255

Tyr Phe Ser Phe Leu Val Lys Asn Ile Ala Arg Leu Val Leu Gln Ala
            260                 265                 270

Tyr Ala Gly Gly Leu Gly Thr Thr Pro Leu Thr Thr Ile Ala Asn
            275                 280                 285

Leu Glu Gly Glu Ala Leu Arg Arg Glu Leu Gln Asn Leu Glu Ser Gly
        290                 295                 300

Gly Leu Phe Arg Thr Leu Gly Leu Lys Asn Leu Leu Glu Gly Asp Phe
305                 310                 315                 320

Phe Ala Trp Tyr Leu Asp Ala Trp Asn Pro Glu Val Glu Glu Ala Leu
                325                 330                 335

Arg Gln Val Leu Ala Arg Leu Ala Glu Tyr Asn Pro Ala Thr Val Gln
            340                 345                 350

Asp Asp Pro His Ser Ala Arg Asp Leu Leu Lys Lys Leu Tyr His Tyr
            355                 360                 365

Leu Leu Pro Arg Asp Ile Arg His Asp Leu Gly Glu Phe Tyr Thr Pro
        370                 375                 380

Asp Trp Leu Ala Glu Arg Leu Leu Asn Gln Leu Gly Glu Pro Trp Phe
385                 390                 395                 400

Ile Met Pro Pro Gly Asn His Pro Pro Arg Gly Leu Pro Asp Lys Arg
                405                 410                 415

Leu Leu Asp Pro Ala Cys Gly Ser Gly Thr Phe Pro Val Leu Ala Ile
            420                 425                 430

Arg Ala Leu Lys Val Asn Cys Phe Leu Ala Gly Phe Ser Glu Ala Asp
        435                 440                 445

Thr Leu Glu Val Ile Leu Asn Ser Val Val Gly Ile Asp Leu Asn Pro
        450                 455                 460

Leu Ala Val Thr Ala Ala Arg Val Asn Tyr Leu Leu Ala Ile Ala Asp
465                 470                 475                 480

Leu Leu Pro Tyr Arg Arg Glu Val Glu Ile Pro Val Tyr Leu Ala
                485                 490                 495

Asp Ser Ile Leu Thr Pro Ala Arg Gly Glu Gly Leu Phe Ala Gln Asn
            500                 505                 510

Arg Arg Ile Leu Glu Thr Ala Val Gly Pro Leu Pro Val Pro Glu Val
        515                 520                 525

Ile Asn Ser Arg Ala Lys Met Glu Arg Leu Thr Asp Leu Leu Glu Glu
        530                 535                 540

Tyr Val Arg Gly Asp Phe Ser Thr Glu Ala Phe Leu Ala Arg Ala Lys
545                 550                 555                 560

Lys Glu Ile Pro Asp Leu Ala Asp Ala Leu His Ala Asp Glu Val Ile
                565                 570                 575

Thr Gly Leu Tyr Glu Arg Leu Arg Asp Leu His Arg Gln Gly Leu Asp
            580                 585                 590

Gly Ile Trp Ala Arg Val Leu Lys Asn Ala Phe Met Pro Leu Phe Leu
            595                 600                 605

Glu Pro Phe Asp Tyr Val Val Gly Asn Pro Pro Trp Ile Asn Trp Glu
```

-continued

```
            610                 615                 620
Ser Leu Pro Gln Ala Tyr Arg Glu Gln Thr Ala Glu Leu Trp Thr Cys
625                 630                 635                 640

Tyr Gly Leu Phe Val His Ser Gly Met Asp Thr Ile Leu Gly Lys Gly
                645                 650                 655

Lys Lys Asp Ala Ser Thr Leu Met Thr Tyr Ala Val Ala Asp Arg Phe
                660                 665                 670

Leu Lys Glu Gly Gly Lys Leu Gly Phe Leu Ile Thr Gln Ser Val Trp
                675                 680                 685

Lys Thr Gly Ala Gly Gln Gly Phe Arg Arg Phe Arg Ile Gly Glu Asn
690                 695                 700

Gly Pro His Leu Arg Val Leu His Val Asp Asp Leu Ser Ser Leu Gln
705                 710                 715                 720

Val Phe Glu Gly Ala Ser Thr Arg Thr Ser Ala Phe Val Leu Gln Lys
                725                 730                 735

Gly Arg Pro Pro Arg Tyr Pro Val Pro Tyr Thr Tyr Trp Lys Lys Thr
                740                 745                 750

Thr Lys Gly Glu Gly Leu Asp Tyr Asp Ser Thr Leu Gly Glu Val Met
                755                 760                 765

Glu Gln Thr Lys Arg Leu Arg Phe His Ala Val Pro Val Asp Pro Asp
                770                 775                 780

Asp Leu Thr Ser Pro Trp Leu Thr Ala Arg Arg Ala Leu Tyr Ser
785                 790                 795                 800

Val Arg Lys Val Leu Gly Thr Ser Glu Tyr Arg Ala Tyr Glu Gly Ala
                805                 810                 815

Asn Ser Gly Gly Ala Asn Gly Ile Tyr Trp Leu Glu Ile Leu Ala Glu
                820                 825                 830

Arg Pro Asp Gly Leu Val Val Arg Asn Val Thr Glu Gly Ala Lys
                835                 840                 845

Arg Glu Val Glu Gly Ile Thr Thr Glu Leu Glu Pro Asp Leu Leu Tyr
                850                 855                 860

Pro Leu Leu Arg Gly Arg Asp Val Arg Arg Trp Tyr Ala Gln Pro Ser
865                 870                 875                 880

Leu His Ile Leu Met Val Gln Asp Pro Lys Thr Arg Arg Gly Ile Asp
                885                 890                 895

Glu Gln Val Leu Gln Lys Arg Tyr Pro Lys Thr Trp Ala Tyr Leu Lys
                900                 905                 910

Arg Phe Glu Ala Val Leu Arg Glu Arg Ser Gly Phe Arg Arg Tyr Phe
                915                 920                 925

Thr Arg Lys Asp Arg Asn Gly Arg Met Val Glu Thr Gly Pro Phe Tyr
                930                 935                 940

Ser Met Phe Asn Val Gly Asp Tyr Thr Phe Ala Pro Trp Lys Val Val
945                 950                 955                 960

Trp Arg Tyr Val Ala Ser Asp Phe Ile Val Ala Val Gly Pro Ala
                965                 970                 975

Ser Asp Glu Lys Pro Val Val Pro Asn Glu Lys Leu Met Leu Val Pro
                980                 985                 990

Val Glu Asp Asp Asn Glu Ala Phe Tyr Leu Cys Gly Val Leu Asn Ser
                995                 1000                1005

Ser Pro Ile Arg Phe Ala Val Gln Ser Phe Phe Val Gln Thr Gln
    1010                1015                1020

Ile Ala Pro His Val Leu Gln Lys Leu Cys Ile Pro Arg Tyr Glu
    1025                1030                1035
```

```
Pro Asn Thr Asp His Gln Asn Arg Ile Ala His Leu Ser Arg Arg
    1040            1045                1050

Ala His Glu Leu Ala Pro Ala Tyr Asn Gly Asp Lys Ala Ala
    1055            1060                1065

Arg Ala Glu Leu Arg Arg Val Glu Glu Glu Ile Asp Arg Ala Ala
    1070            1075                1080

Ala Gln Leu Trp Gly Leu Thr Glu Glu Glu Leu Ala Glu Ile Arg
    1085            1090                1095

Arg Ser Leu Glu Glu Leu Arg Gly
    1100            1105

<210> SEQ ID NO 23
<211> LENGTH: 20
<212> TYPE: PRT
<213> ORGANISM: Unknown
<220> FEATURE:
<223> OTHER INFORMATION: amino acid derived from sequencing the
      N-terminus of Tth111II

<400> SEQUENCE: 23

Met Ser Asn Trp Ile Asp Leu Tyr Thr His Leu Lys Gln Glu Val Pro
1               5                   10                  15

Trp Phe Phe Asn
            20

<210> SEQ ID NO 24
<211> LENGTH: 32
<212> TYPE: DNA
<213> ORGANISM: Unknown
<220> FEATURE:
<223> OTHER INFORMATION: primers
<220> FEATURE:
<221> NAME/KEY: misc_feature
<222> LOCATION: (15)..(15)
<223> OTHER INFORMATION: Y = C or T
<220> FEATURE:
<221> NAME/KEY: misc_feature
<222> LOCATION: (21)..(21)
<223> OTHER INFORMATION: H = A or C or T
<220> FEATURE:
<221> NAME/KEY: misc_feature
<222> LOCATION: (24)..(24)
<223> OTHER INFORMATION: Y = C or T
<220> FEATURE:
<221> NAME/KEY: misc_feature
<222> LOCATION: (27)..(27)
<223> OTHER INFORMATION: N = A, G, C or T
<220> FEATURE:
<221> NAME/KEY: misc_feature
<222> LOCATION: (30)..(30)
<223> OTHER INFORMATION: Y = C or T

<400> SEQUENCE: 24
ggtggtggat ccaaytggat hgayctntay ac                           32

<210> SEQ ID NO 25
<211> LENGTH: 36
<212> TYPE: DNA
<213> ORGANISM: Thermus thermophilus 111
<220> FEATURE:
<221> NAME/KEY: misc_feature
<222> LOCATION: (13)..(13)
<223> OTHER INFORMATION: R = A or G
<220> FEATURE:
<221> NAME/KEY: misc_feature
<222> LOCATION: (16)..(16)
<223> OTHER INFORMATION: R = A or G
<220> FEATURE:
```

```
<221> NAME/KEY: misc_feature
<222> LOCATION: (19)..(19)
<223> OTHER INFORMATION: R = A or G
<220> FEATURE:
<221> NAME/KEY: misc_feature
<222> LOCATION: (23)..(23)
<223> OTHER INFORMATION: N = A, G, C or T
<220> FEATURE:
<221> NAME/KEY: misc_feature
<222> LOCATION: (25)..(25)
<223> OTHER INFORMATION: N = A, G, C or T
<220> FEATURE:
<221> NAME/KEY: misc_feature
<222> LOCATION: (28)..(28)
<223> OTHER INFORMATION: N = A, G, C or T
<220> FEATURE:
<221> NAME/KEY: misc_feature
<222> LOCATION: (31)..(31)
<223> OTHER INFORMATION: Y = C or T
<220> FEATURE:
<221> NAME/KEY: misc_feature
<222> LOCATION: (34)..(34)
<223> OTHER INFORMATION: Y = C or T

<400> SEQUENCE: 25
ggtggtggat ccrttraara accanggnac ytcytg                                   36

<210> SEQ ID NO 26
<211> LENGTH: 26
<212> TYPE: DNA
<213> ORGANISM: Unknown
<220> FEATURE:
<223> OTHER INFORMATION: primer
<220> FEATURE:
<221> NAME/KEY: misc_feature
<222> LOCATION: (15)..(15)
<223> OTHER INFORMATION: R = A or G
<220> FEATURE:
<221> NAME/KEY: misc_feature
<222> LOCATION: (18)..(18)
<223> OTHER INFORMATION: N = A, G, C or T
<220> FEATURE:
<221> NAME/KEY: misc_feature
<222> LOCATION: (21)..(21)
<223> OTHER INFORMATION: N = A, G, C or T

<400> SEQUENCE: 26
acccatctaa aacargtncc ntggtt                                              26

<210> SEQ ID NO 27
<211> LENGTH: 29
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (15)..(15)
<223> OTHER INFORMATION: R = A or G
<220> FEATURE:
<221> NAME/KEY: misc_feature
<222> LOCATION: (18)..(18)
<223> OTHER INFORMATION: N = A, G, C or T
<220> FEATURE:
<221> NAME/KEY: misc_feature
<222> LOCATION: (21)..(21)
<223> OTHER INFORMATION: R = A or G
<220> FEATURE:
<221> NAME/KEY: misc_feature
<222> LOCATION: (24)..(24)
<223> OTHER INFORMATION: D = A, G or T

<400> SEQUENCE: 27
tgttttagat gggtrtanag rtcdatcca                                           29
```

<210> SEQ ID NO 28
<211> LENGTH: 24
<212> TYPE: DNA
<213> ORGANISM: Unknown
<220> FEATURE:
<223> OTHER INFORMATION: primer

<400> SEQUENCE: 28
accggactct acgagaggtt gcgc                                          24

<210> SEQ ID NO 29
<211> LENGTH: 24
<212> TYPE: DNA
<213> ORGANISM: Unknown
<220> FEATURE:
<223> OTHER INFORMATION: primer

<400> SEQUENCE: 29
gtcggcatgg agggcatcgg ccag                                          24

<210> SEQ ID NO 30
<211> LENGTH: 24
<212> TYPE: DNA
<213> ORGANISM: unknown
<220> FEATURE:
<223> OTHER INFORMATION: primer

<400> SEQUENCE: 30
ggacaggaac ggaccgcatg gtgg                                          24

<210> SEQ ID NO 31
<211> LENGTH: 24
<212> TYPE: DNA
<213> ORGANISM: Unknown
<220> FEATURE:
<223> OTHER INFORMATION: primer

<400> SEQUENCE: 31
tagcgcctga agccggaacg ctcc                                          24

<210> SEQ ID NO 32
<211> LENGTH: 69
<212> TYPE: DNA
<213> ORGANISM: Unknown
<220> FEATURE:
<223> OTHER INFORMATION: primers

<400> SEQUENCE: 32
ggtggttcta gaaataattt tgtttaactt taaggaggta aatagaactg gatcgatctt    60
tacacccat                                                           69

<210> SEQ ID NO 33
<211> LENGTH: 36
<212> TYPE: DNA
<213> ORGANISM: unknown
<220> FEATURE:
<223> OTHER INFORMATION: primer

<400> SEQUENCE: 33
ggtggtggat ccctaccccc gcaactcctc caaact                             36

<210> SEQ ID NO 34
<211> LENGTH: 14
<212> TYPE: DNA

-continued

```
<213> ORGANISM: Unknown
<220> FEATURE:
<223> OTHER INFORMATION: mutant copy

<400> SEQUENCE: 34
gtggatcgat cttt                                                    14
```